US008952188B2

(12) United States Patent
Ivanov et al.

(10) Patent No.: US 8,952,188 B2
(45) Date of Patent: Feb. 10, 2015

(54) GROUP 4 METAL PRECURSORS FOR METAL-CONTAINING FILMS

(75) Inventors: Sergei Vladimirovich Ivanov, Schnecksville, PA (US); Xinjian Lei, Vista, CA (US); Hansong Cheng, Singapore (SG); Daniel P. Spence, Carlsbad, CA (US); Moo-Sung Kim, Sungnam (KR)

(73) Assignee: Air Products and Chemicals, Inc., Allentown, PA (US)

( * ) Notice: Subject to any disclaimer, the term of this patent is extended or adjusted under 35 U.S.C. 154(b) by 622 days.

(21) Appl. No.: 12/904,421

(22) Filed: Oct. 14, 2010

(65) Prior Publication Data

US 2011/0250126 A1 Oct. 13, 2011

Related U.S. Application Data

(60) Provisional application No. 61/254,253, filed on Oct. 23, 2009.

(51) Int. Cl.
*C23C 16/18* (2006.01)
*C23C 16/40* (2006.01)
*C23C 16/455* (2006.01)

(52) U.S. Cl.
CPC .................. *C23C 16/18* (2013.01); *C17F 7/006* (2013.01); *C23C 16/405* (2013.01); *C23C 16/45553* (2013.01)
USPC ........... 556/54; 556/51; 423/610; 106/287.19

(58) Field of Classification Search
None
See application file for complete search history.

(56) References Cited

U.S. PATENT DOCUMENTS

| | | | |
|---|---|---|---|
| 6,117,487 A | 9/2000 | Akutsu et al. | |
| 6,383,669 B1 * | 5/2002 | Leedham et al. | 428/702 |
| 6,562,990 B1 | 5/2003 | St. Clair et al. | |
| 6,603,033 B2 | 8/2003 | Woo | |
| 7,691,984 B2 | 4/2010 | Lei et al. | |
| 7,723,493 B2 | 5/2010 | Lei et al. | |
| 2007/0219299 A1 | 9/2007 | Okamoto et al. | |
| 2007/0248754 A1 | 10/2007 | Lei et al. | |
| 2008/0254218 A1 | 10/2008 | Lei et al. | |
| 2008/0315295 A1 | 12/2008 | Ji et al. | |
| 2009/0136685 A1 | 5/2009 | Lei et al. | |
| 2009/0181549 A1 | 7/2009 | Yoneda et al. | |
| 2010/0018439 A1 | 1/2010 | Cameron et al. | |
| 2010/0119726 A1 | 5/2010 | Lei et al. | |
| 2010/0143607 A1 | 6/2010 | Lei et al. | |

FOREIGN PATENT DOCUMENTS

| | | |
|---|---|---|
| CN | 1394221 A | 1/2003 |
| CN | 101330014 A | 12/2008 |
| JP | 63-056530 A | 3/1988 |
| JP | 2822946 | 10/1997 |
| JP | 10114781 | 5/1998 |
| JP | 2007-197804 A2 | 1/2006 |
| JP | 2006076943 A * | 3/2006 |
| JP | 2007197804 A * | 8/2007 |
| JP | 2007197804 | 9/2007 |
| JP | 2009170439 A | 7/2009 |
| KR | 200280361 Y1 | 7/2002 |
| KR | 2002-80361 | 10/2002 |
| TW | 200902759 A | 1/2009 |
| WO | 8403042 | 8/1984 |
| WO | 9640690 | 12/1996 |
| WO | 01/49789 A2 | 7/2001 |
| WO | 2005/108492 | 11/2005 |
| WO | WO 2005108492 A1 * | 11/2005 |

OTHER PUBLICATIONS

Urmila Patil, M. Sc.: "precursors for metal organic chemical vapor deposition (MOCVD) f ZrO2 and HfO2 thin films as gate dielectrics in complementary metal-oxide-semiconductor (CMOS) devices," Dissertation submitted for the degree of Dr. rer. Nat. (Doctor rerum naturalium) in the faculty of Chemistry at the Ruhr-University Bochum, Germany, 2005, http://www-brs.ub.ruhr-uni-cochum.de/netahtml/HSS/Diss/PatilUrmila/diss.pdf (Figs 8-10, p. 152).

Byoung-Jae Bae et al., "Preparation of Anatase TiO2 Thin Films with (O'Pr)2Ti(CH3COCHCONEt2)2 Precursor by MOCVD," Bull. Korean Chem. Soc., 2004, vol. 25, No. 11, pp. 1661-1666.

R. Bhakta et al., "MOCVD of TiO2 thin films using a new class of metalorganic precursors," Electrochemical Society Proceedings, vol. 2003-08, Jan. 1, 2003, pp. 1477-1483.

Urmila Patil; "Precursors for Metal Organic Chemical Vapor Deposition (MOCVD) of ZrO2 and HfO2 Thin Films as Gate Dielectrics in Complementary Metal-Oxide-Semiconductor (CMOS) Devices"; Dissertation submitted for the degree of Dr.Rerum Naturalium in the faculty of Chemistry at the Ruhr-University Bochum; Dec. 31, 2005.

Saxena, U.B., et al; "Reactions of Zirconium Isopropoxide with .beta.-diketones and .beta.-keto-esters"; Journals of the Chemical Society; No. 6; Jan. 1, 1970; pp. 904-907; XP009147959.

(Continued)

*Primary Examiner* — Sudhakar Katakam
(74) *Attorney, Agent, or Firm* — Rosaleen P. Morris-Oskanian

(57) ABSTRACT

The present invention is related to a family of Group 4 metal precursors represented by the formula:

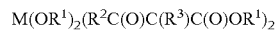

$M(OR^1)_2(R^2C(O)C(R^3)C(O)OR^1)_2$ wherein M is a Group 4 metals of Ti, Zr, or Hf; wherein $R^1$ is selected from the group consisting of a linear or branched $C_{1-10}$ alkyl and a $C_{6-12}$ aryl, preferably methyl, ethyl or n-propyl; $R^2$ is selected from the group consisting of branched $C_{3-10}$ alkyls, preferably iso-propyl, tert-butyl, sec-butyl, iso-butyl, or tert-amyl and a $C_{6-12}$ aryl; $R^3$ is selected from the group consisting of hydrogen, $C_{1-10}$ alkyls, and a $C_{6-12}$ aryl, preferably hydrogen. In a preferred embodiment of this invention, the precursor is a liquid or a solid with a melting point below 60° C.

13 Claims, 9 Drawing Sheets

(56) References Cited

OTHER PUBLICATIONS

Pal, M., et al; "Reactions of Titanium(IV) Isopropoxide with Aliphatic and Aromatic Hydroxy Esters, Part I. 5-, 6-, 7- and 8-Coordinate Titanium(IV) Complexes"; Transition Metal Chemistry, Chapman & Hall, GB; vol. 3, No. 4; Jan. 1, 1978; pp. 225-229; XP009147958.

Trundle, C., et al; "Precursors for Thin Film Oxides by Photo-MOCVD"; Applied Surface Science, Elsevier, Amsterdam, NL; vol. 36, No. 1-4; Jan. 1, 1989; pp. 102-118; XP024720798.

Bae Byoung-Jae, et al; "Preparatin of Anatase TiO2 Thin Films with (OiPr)2T1(CH3COCHCONEt2)2 Precursor by MOCVD"; Bulletin of the Korean Chemical Society; vol. 25, No. 11; Nov. 20, 2004; pp. 1661-1666; XP009147972.

Bhakta, R., et al; "MOCVD of TiO2 Thin Films Using a New Class of Metalorganic Precursors"; Proceedings—Electrochemical Society, Pennington, NJ; vol. 2003-8; Jan. 1, 2003; pp. 1477-1483; XP009147967.

B. Bae, et al, Preparation of Anatase TiO2 Thin Films with (OiPr)2Ti(CH3COCHCONEt2)2 Precursor by MOCVD, Bull. Korean Chem. Soc., 2004, 1661-1666.

R. Bhakta, et al, Monocuclear Mixed B-Ketoester-alkoxide Compound of Titanium as a Promising Precursor for Low-Temperature MOCVD of TiO2 Thin Films, Chemical Vapor Deposition, 2003, 295-298.

D.M. Puri, et al, Derivatives of Titanium with Compounds Having Bidentate Ligands II. Reactions of Titanium Alkoxides with Methyl Acetoacetate, Journal of the Less-Common Metals, 1961, 253-258.

A. Yamamoto, et al, Structures of the Reaction Products of Tetraalkoxytitanium with Acetylacetone and Ethyl Acetoacetate, J. Am. Chem. Soc., 1957, 4344-4348.

U.B. Saxena, et al, Reactions of Zirconium Isopropoxide with B-Diketones and B-Keto-esters, J. Chem. Soc., 1970, 904-907.

A. Baunemann, et al, Mononuclear precursor for MOCVD of HfO2 thin films, Chem. Commun., 2004, 1610-1611.

R. Bhakta, et al, MOCVD of TiO2 thin films and studies on the nature of molecular mechanisms involved in the decomposition of [Ti(OPri)2(tbaoac)2], Journal of Materials Chemistry, 2004, 3231-3238.

U. Patil, et al, MOCVD of ZrO2 and HfO2 Thin Films from Modified Monomeric Precursors, Chemical Vapor Deposition, 2006, 172-180.

F. Gornshtein, et al, Titanium and Zirconium Complexes for Polymerization of Propylene and Cyclic Esters, Organometallics, 2007, 497-507.

B.C. Kang, et al, Selective MOCVD of titanium oxide and zirconium oxide thin films using single molecular precursors on Si(1 0 0) substrates, Journal of Physics and Chemistry of Solids, 2008, 128-132.

U. Patil, et al, Synthesis and structure of mixed isopropoxide—B-ketoester and B-ketoamide zirconium complexes: Potential precursors for MOCVD of ZrO2, Journal of Materials Chemistry, 2003, 2177-2184.

R. Thomas, et al, Liquid injection MOCVD of TiO2 and SrTiO3 thin films from [Ti(OPri)2 (tbaoac)2]: Film properties and compatibility with [Sr(thd)2], Surface & Coatings Technology, 2007, 9135-9140.

K. Woo, et al, Novel Titanium Compounds for Metal-Organic Chemical Vapor Deposition of Titanium Dioxide Films with an Ultrahigh Deposition Rate, Inorganic Chemistry, 2003, 2378-2383.

\* cited by examiner

GROUP 4 METAL PRECURSORS FOR METAL-CONTAINING FILMS

CROSS REFERENCE TO RELATED APPLICATION

The present patent application claims the benefit of U.S. Provisional Patent Application Ser. No. 61/254,253 filed Oct. 23, 2009.

BACKGROUND OF THE INVENTION

With each generation of metal oxide semiconductor (MOS) integrated circuits (IC), device dimensions have been continuously scaled down to provide for high-density and high-performance, such as high speed and low power consumption requirements. Unfortunately, field effect semiconductor devices produce an output signal that is proportional to the width of the channel, such that scaling reduces their output. This effect has generally been compensated for by decreasing the thickness of the gate dielectric, thus bringing the gate in closer proximity to the channel and enhancing the field effect, which thereby increases the drive current. Therefore, it has become increasingly important to provide extremely thin, reliable and low-defect gate dielectrics for improving device performance.

For decades, a thermal silicon oxide, $SiO_2$ has been the primary gate dielectric, because it is compatible with the underlying silicon substrate, and its fabrication process is relatively simple. However, because the silicon oxide gate dielectric has a relatively low dielectric constant (k), 3.9, further scaling down of silicon oxide gate dielectric thickness to less than 10 Å has become more and more difficult, especially due to gate-to-channel leakage current through the thin silicon oxide gate dielectric.

This leads to consideration of alternative dielectric materials, which can be formed in a thicker layer than silicon oxide, but still produce the same or better device performance. This performance can be expressed as "equivalent oxide thickness (EOT)". Although the alternative dielectric material layer may be thicker than a comparative silicon oxide layer, it has the equivalent effect of a much thinner layer of a silicon oxide layer.

To this end, high-k metal oxide materials have been proposed as the alternative dielectric materials for gate or capacitor dielectrics. Group 4-containing precursors may also be used by themselves or combined with other metal-containing precursors to make high dielectric constant and/or ferroelectric oxide thin films such as, for example, $Pb(Zr,Ti)O_3$ or $(Ba,Si)(Zr,Ti)O_3$. Because the dielectric constant of metal oxide materials can be made greater than that of the silicon oxide, a thicker metal oxide layer having a similar EOT can be deposited. As a result, the semiconductor industry requires Group 4 precursors, such as, for example, titanium-containing, zirconium-containing, and hafnium-containing precursors and combinations thereof, to be able to deposit metal-containing films such as, but not limited to, oxide, nitride, silicate or combinations thereof on substrates, such as metal nitride or silicon.

Unfortunately, the use of high-k metal oxide materials presents several problems, when using traditional substrate materials, such as silicon. The silicon can react with the high-k metal oxide or be oxidized during deposition of the high-k metal oxide or subsequent thermal processes, thereby forming an interface layer of silicon oxide. This increases the equivalent oxide thickness, thereby degrading device performance. Further, an interface trap density between the high-k metal oxide layer and the silicon substrate is increased. Thus, the channel mobility of the carriers is reduced. This reduces the on/off current ratio of the MOS transistor, thereby degrading its switching characteristics. Also, the high-k metal oxide layer, such as a hafnium oxide ($HfO_2$) layer or a zirconium oxide ($ZrO_2$) layer, has a relatively low crystallization temperature and is thermally unstable. Thus, the metal oxide layer can be easily crystallized during a subsequent thermal annealing process for activating the dopants injected into source/drain regions. This can form grain boundaries in the metal oxide layer, through which current can pass. As the surface roughness of the metal oxide layer increases, the leakage current characteristics may deteriorate. Further, the crystallization of the high-k metal oxide layer undesirably affects a subsequent alignment process due to irregular reflection of the light on an alignment key having the rough surface.

Group 4 metal-containing films can be deposited using chemical vapor deposition (CVD) and/or atomic layer deposition (ALD) processes. In a traditional CVD process the vapors of one or more volatile precursors are introduced into a chemical vapor deposition reactor loaded with a semi-fabricated substrate, which has been pre-heated to the temperature above the thermal decomposition of at least one of the precursors. The rate of film growth is determined by the rate of reaction between the reactants on the surface, and the film growth continues, as long as reactant vapors are present in the vapor phase. On the other hand, in an atomic layer deposition (ALD) process, reactants are introduced into an ALD reactor sequentially, thus avoiding any gas phase reactions between the reactants. A typical cycle of ALD processes for deposition metal oxide films includes: 1) introducing enough vapors of a metal containing precursor to the ALD chamber to allow the precursor to chemically adsorb on the surface until the whole surface area is covered; 2) purging the ALD chamber with inert gas to remove any by-products as well as unreacted precursors; 3) introducing an oxidizer to react with the precursor adsorbed on the surface; 4) purging away any unreacted oxidizer and any reaction by-products. The cycle is repeated until a desired thickness is achieved. An ideal ALD process is self-limiting, i.e. the substrate surface is saturated with a reactant during its introduction and the film growth stops even though large excess of precursors are present in the gas phase. Therefore, ALD provides multiple advantages over CVD for deposition of highly conformal films on complex surfaces, such as deep trenches and other stepped structures The balance between good thermal stability of ALD precursors and the ability of ALD precursors to chemisorb on the substrate surface is very important for producing thin, conformal films of high K dielectric metal oxides. It is desirable that the precursors are thermally stable during vapor delivery in order to avoid premature decomposition of the precursor, before it reaches the vapor deposition chamber during processing. Premature decomposition of the precursor, not only results in undesirable accumulation of side products that would clog fluid flow conduits of the deposition apparatus, but also may cause undesirable variations in composition or as well as dielectric constant and/or ferroelectric properties of the deposited metal oxide thin film.

A number of various delivery systems have been developed for the delivery of precursors to CVD or ALD reactors. For example, in direct liquid injection (DLI) method a liquid precursor or a solution of a precursor in a solvent is delivered to a heated vaporization system, whereby the liquid composition is transferred from the liquid phase into the gas phase. Advanced liquid metering of the precursor to the vaporizer provides accurate, stable control of precursor delivery rate.

However, it is critical during the vaporization process that the precursor structure is maintained and decomposition is eliminated. Another method, which is already widely used in semiconductor industry for delivery of metal organic precursors, is based on conventional bubbler technology, where inert gas is bubbled through a neat liquid or a molten precursor at elevated temperature. Typically, precursors have low vapor pressure and have to be heated to 100-200° C. to deliver enough precursor vapors to the deposition reactor by the bubbling method. Solid precursors delivered from their molten phase may plug the lines during multiple cooling/heating cycles. It is desired that precursors are liquids or solids with melting point significantly lower than the bubbler temperature. Products of thermal decomposition may also plug delivery lines and affect the delivery rate of precursors. Extended periods of time at the bubbler temperatures may also cause thermal decomposition of the precursors. The precursors may also react with traces of moisture and oxygen introduced to the bubbler during multiple deposition cycles. It is highly desirable that the precursors maintain their chemical identity over time during storage and delivery. Any change in chemical composition of a Group 4 precursor is deleterious, because it may impair the ability of the vapor deposition process to achieve constant delivery and film growth.

Prior art in the field of the present invention includes: U.S. Pat. No. 6,603,033; Chem. Vap. Deposition, 9, 295 (2003); J. of Less Common Metals, 3, 253 (1961); J. Am. Chem. Soc. 79, p 4344-4348 (1957); Journal of the Chemical Society A: Inorganic, Physical, and Theoretical Chemistry: 904-907 (1970); Chemical Communications 10(14): 1610-1611 (2004); Journal of Materials Chemistry 14, 3231-3238 (2004); Chemical Vapor Deposition 12, 172-180 (2006); JP2007197804A; JP10114781A; WO1984003042A1; JP2822946B2; U.S. Pat. No. 6,562,990B; WO9640690; US2010/0018439A; and Applicants' co-pending application US2007/0248754A1, U.S. Ser. No. 11/945,678 filed on Nov. 27, 2007, Applicants' co-pending application U.S. Ser. No. 12/266,806 which was filed on Nov. 11, 2008, Applicants' co-pending application US 2010/0143607 A1, U.S. Ser. No. 12/629,416 filed on Dec. 2, 2009, or Applicants' U.S. Pat. No. 7,691,984, U.S. Pat. No. 7,723,493.

As previously discussed, the Group 4 precursors in the prior art are mostly solid and have relatively low vapor pressure (e.g., 0.5 torr or below at the delivery temperature). Of a few Group 4 precursors that are in liquid form in the prior art, these precursors are not thermally stable at temperatures greater than 150° C., thus causing delivery or process issues during semiconductor manufacturing, which can include, but are not limited to, lower ALD process window, clogging of the delivery lines between the source container and reactor, and particle deposition on the wafers.

Accordingly, there is a need to develop Group 4 precursors, preferably liquid Group 4 precursors, which exhibit at least one of the following properties: lower molecular weight (e.g., 500 m.u. or below), lower melting point (e.g., 60° C. or below), high vapor pressure (e.g., 0.5 torr or greater). Group 4 precursors having high ALD thermal window (e.g., 300° C. and above) as well as high ALD growth rate (e.g. above 0.3 A/cycle) are also needed. There is also a need to develop Group 4 precursors which are thermally stable and which maintain their chemical composition during storage and delivery.

BRIEF SUMMARY OF THE INVENTION

The present invention is a family of Group 4 metal precursors represented by the formula: $M(OR^1)(R^2C(O)C(R^3)C(O)OR^1)_2$; also illustrated schematically as:

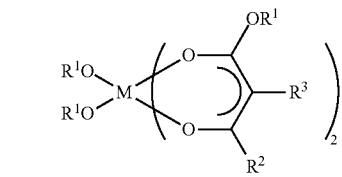

wherein M is a Group 4 metal selected from the group consisting of Ti, Zr, and Hf; wherein $R^1$ is selected from the group consisting of a linear or branched alkyl group containing 1 to 10 carbon atoms and an aryl containing 6 to 12 carbon atoms, preferably methyl, ethyl, and n-propyl when M is Ti; $R^2$ can be selected from the group consisting of branched $C_{3-10}$ alkyls, preferably iso-propyl, tert-butyl, sec-butyl, iso-butyl, tert-amyl, and a $C_{6-12}$ aryl; $R^3$ is selected from the group consisting of hydrogen, $C_{1-10}$ alkyls, and a $C_{6-12}$ aryl, preferably hydrogen and methyl.

In a preferred embodiment of this invention, the precursor is a liquid or a solid with melting point below 60° C.

The advantage of these precursors is that they are thermally stable in the liquid phase, up to at least 200° C., and that they allow deposition of highly conformal metal oxide films by atomic layer deposition or cyclic chemical vapor deposition above 300° C.

titanium and bis(n-propoxy)bis(n-propyl 4,4-dimethyl-3-oxopentanoato)titanium (bottom). The presence of two methoxide signals in the $^1$H NMR spectra of the mixture (bottom) suggests intermolecular ligand exchange of methoxy and n-propoxy ligands between the two complexes to result in at least two new complexes having methoxy, n-propoxy, as well as n-propyl 4,4 dimethyl-3-oxopentanoate ligand and methoxy, n-propoxy as well as methyl 4,4 dimethyl-3-oxopentanoate ligand.

Figure 6:
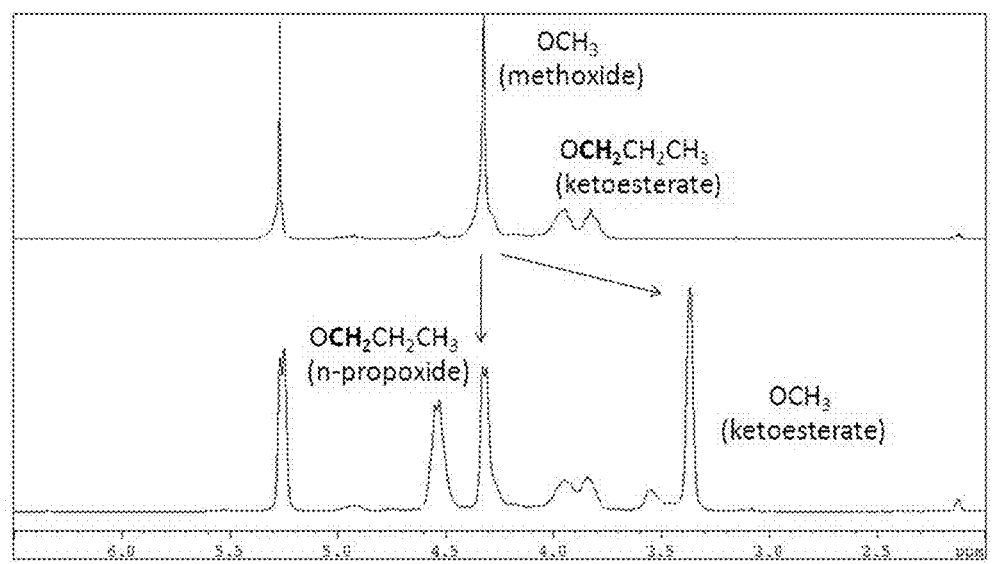

FIG. 6 shows $^1$H NMR spectra of d$^8$-toluene solutions of bis(methoxy)bis(n-propyl 4,4-dimethyl-3-oxopentanoato)titanium (top) and bis(methoxy)bis(n-propyl 4,4-dimethyl-3-oxopentanoato)titanium heated neat for one hour at 200° C. (top), mixed alkoxy. Presence of at least two sets of OCH$_3$ groups (attributed to methoxy and methyl 4,4-dimethyl-3-oxopentanoato ligands) and at least two sets of (OCH$_2$CH$_2$CH$_3$) groups (attributed to n-propoxy and n-propyl 4,4-dimethyl-3-oxopentanoato ligands) suggests ligand exchange of methoxy and n-propoxy groups between ketoesterate and alkoxy ligands, resulting in the formation of a mixture of precursors.

Figure 7:
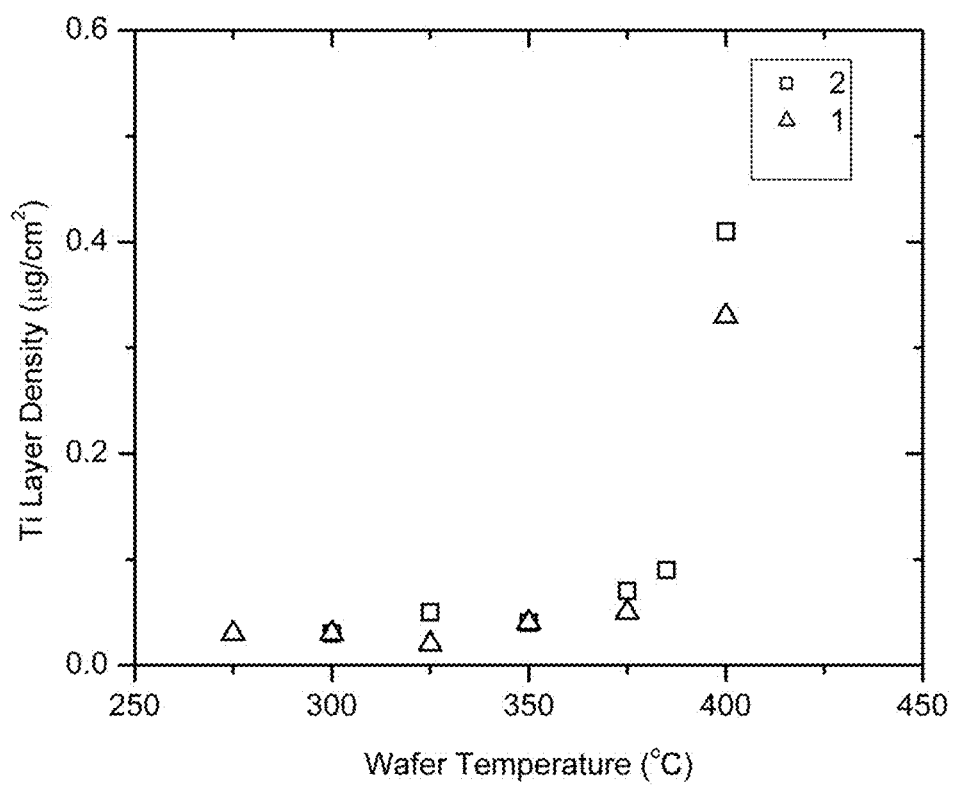

FIG. 7 is the temperature dependence of thermal surface reactivity of bis(methoxy)bis(methyl 4,4-dimethyl-3-oxopentanoato)titanium (1) and bis(ethoxy)bis(ethyl 4,4-dimethyl-3-oxopentanoato)titanium (2), indicating that there are no thermal decompositions on the heated substrate surface at a temperature up to 350° C.

Figure 8:
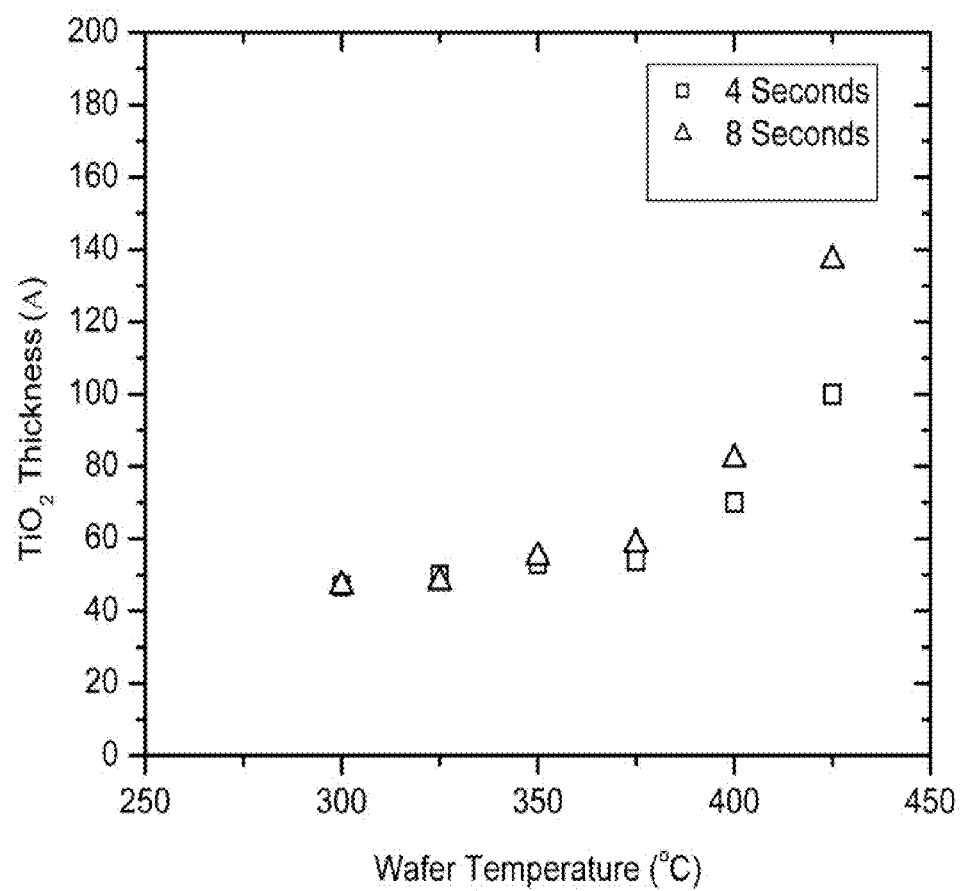

FIG. 8 is the temperature dependence of the thermal ALD of titanium oxide film using 100 ALD cycles of ozone and bis(ethoxy)bis(ethyl 4,4-dimethyl-3-oxopentanoato)titanium, indicating that ALD thermal window for this precursor is at least up to ~375° C.

Figure 9:
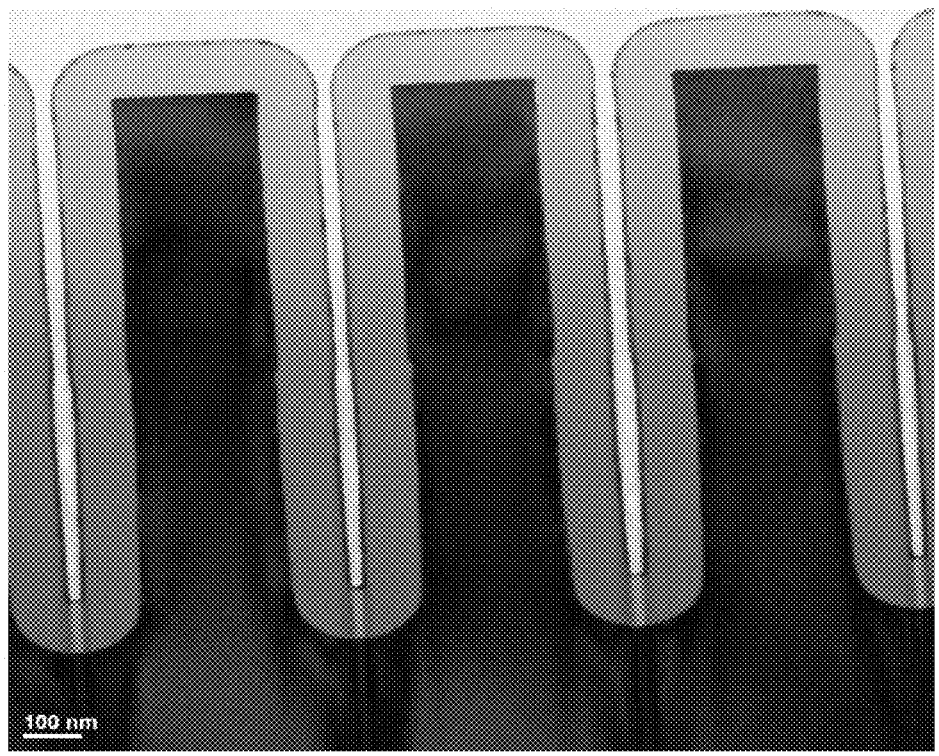

FIG. 9 is a Transmission Electron Microscope (TEM) image of the deposited TiO$_2$ film on a patterned substrate employing bis(ethoxy)bis(ethy 4,4-dimethyl-3-oxopentanoato)titanium as liquid titanium precursor, demonstrating excellent step coverage (>90%) from the top to the bottom of the patterned substrate.

DETAILED DESCRIPTION OF THE INVENTION

Disclosed herein are liquid or low melting point Group 4 metal precursors that are suitable, for example, as precursors in chemical vapor deposition, cyclical chemical vapor deposition (CCVD) or atomic layer deposition processes. The complexes and compositions are useful for fabricating metal-containing films on substrates, such as silicon, metal nitride, metal oxide, metal oxynitride, metal silicate, and other metal containing layers via chemical vapor deposition (CVD), cyclical chemical vapor deposition (CCVD) or atomic layer deposition (ALD) processes The deposited metal-containing films have applications ranging from computer chips, optical device, magnetic information storage, to metal-containing catalyst coated on a supporting material.

Also disclosed herein are methods for preparing these precursors, as well as their use in vapor deposition processes, particularly cyclic CVD or ALD deposition processes.

A number of Group 4 mixed-ligand metal precursors containing alkoxy, diketonate, ketoesterate, cyclopentadienyl ligands have been proposed for deposition of metal oxide films. Using complexes with different ligands permits the modification of physical properties and chemical reactivity of precursors. However, one potential problem of precursors containing different ligands is that ligand exchange during storage or delivery may result in the formation of a mixture of compounds having different volatility and reactivity. Careful design of the precursor's chemical structure is required to optimize precursor performance in CVD, CCVD or ALD deposition, as well as avoiding potential inter- as well as intra-molecular ligand exchange reactions when delivery is at higher temperature.

The present invention is related to a family of Group 4 metal precursors represented by the formula: M(OR$^1$)$_2$(R$^2$C(O)C(R$^3$)C(O)OR$^1$)$_2$, also depicted in 2-dimensions as:

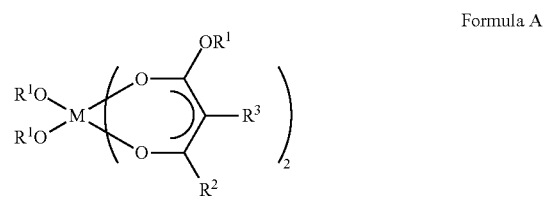

Formula A wherein M is a Group 4 metal selected from the group consisting of Ti, Zr, and Hf; R$^1$ is selected from the group consisting of a linear or branched C$_{1-10}$ alkyl and a C$_{6-12}$ aryl, preferably methyl, ethyl or n-propyl; R$^2$ is selected from the group consisting of branched C$_{3-10}$ alkyls, preferably iso-propyl, tert-butyl, sec-butyl, iso-butyl or tert-amyl and a C$_{6-12}$ aryl; R$^3$ is selected from the group consisting of hydrogen, C$_{1-10}$ alkyls, and a C$_{6-12}$ aryl, preferably hydrogen.

Figure 3:
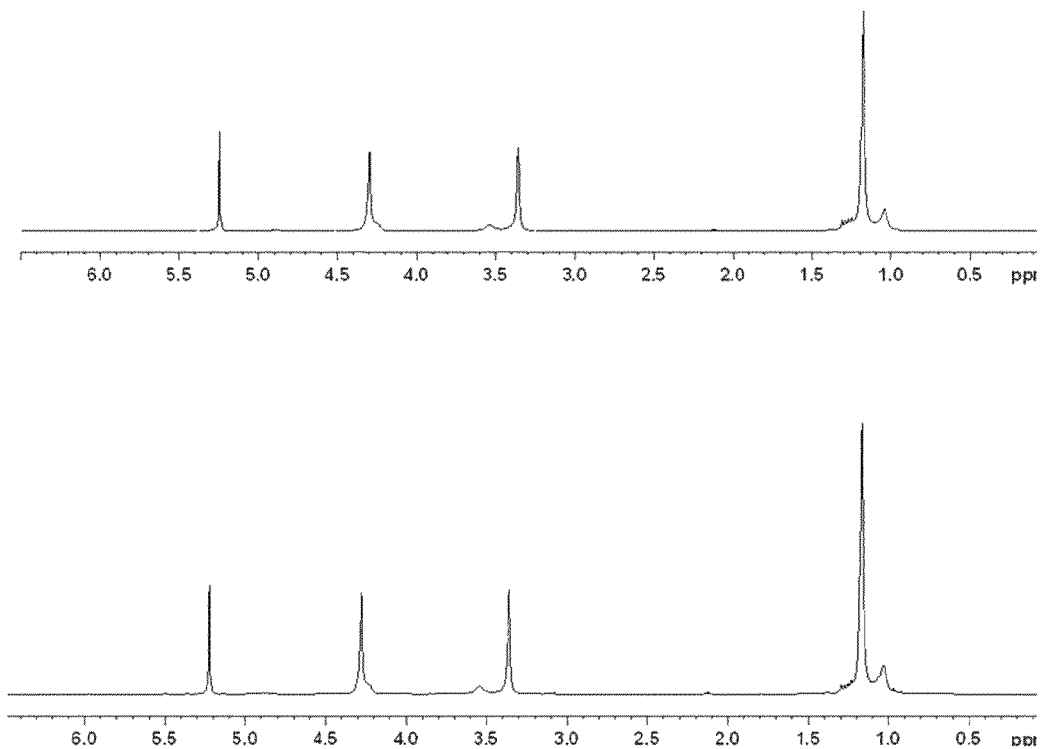
FIG. 3 shows $^1$H NMR (nuclear magnetic resonance) spectra of bis(methoxy)bis(methyl 4,4-dimethyl-3-oxopentanoato)titanium (solutions in $d^8$-toluene) before (top) and after heating for one hour at 200° C. (bottom), indicating no changes in its composition after thermal treatment and showing good thermal stability of this complex.

One unique feature of these precursors, over the other potential precursors in prior art containing both alkoxy and ketoesterate ligands, is that the present invention precursors have only common alkoxy groups, which prevent the formation of other metal precursor complexes at higher temperature by exchange of alkoxy groups among adjacent bonding sites, thus providing good thermal and compositional stability. Good thermal and compositional stability of the precursors is important to ensure consistent precursor delivery to a vapor deposition chamber and consistent vapor deposition parameters. For example, FIG. 3 shows $^1$H NMR spectra of bis(methoxy)bis(methyl 4,4-dimethyl-3-oxopentanoato)titanium before and after heating for one hour at 200° C., indicating no changes in its composition after thermal treatment, and thus, very good thermal stability of this precursor. No changes in $^1$H NMR spectra after heating for one hour at 200° C. were also observed during thermal study of other precursors, where the R$^1$ groups are the same, for example bis(n-propoxy)bis(n-propyl 4,4-dimethyl-3-oxopentanoato) titanium.

In contrast, multiple ligand exchange processes are possible for group 4 metal precursors having different alkoxy groups. Heating up such complexes in a container may result in a mixture of complexes having different composition and volatilities. For example, FIG. 6 shows $^1$H NMR spectra of d$^8$-toluene solutions of bis(methoxy)bis(n-propyl 4,4-dimethyl-3-oxopentanoato)titanium before and after heating for one hour at 200° C. in which there are two kinds of alkoxy groups, i.e. methoxy and n-propoxy. Presence of at least two sets of OCH$_3$ groups (attributed to methoxy and methyl 4,4-dimethyl-3-oxopentanoato ligand) and at least two sets of (OCH$_2$CH$_2$CH$_3$) groups (attributed to n-propoxy and n-propyl 4,4-dimethyl-3-oxopentanoato ligands) suggests ligand exchange of methoxy and n-propoxy groups between ketoesterate and methoxy ligands, and the formation of a mixture of precursors having two different ketoesterate ligands, as shown below. This type of exchange results in metal precursor complexes having the same molecular weight, but different ketoesterate ligands and different volatility and chemical reactivity.

Formula B

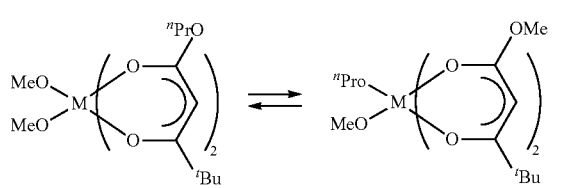

Figure 5:
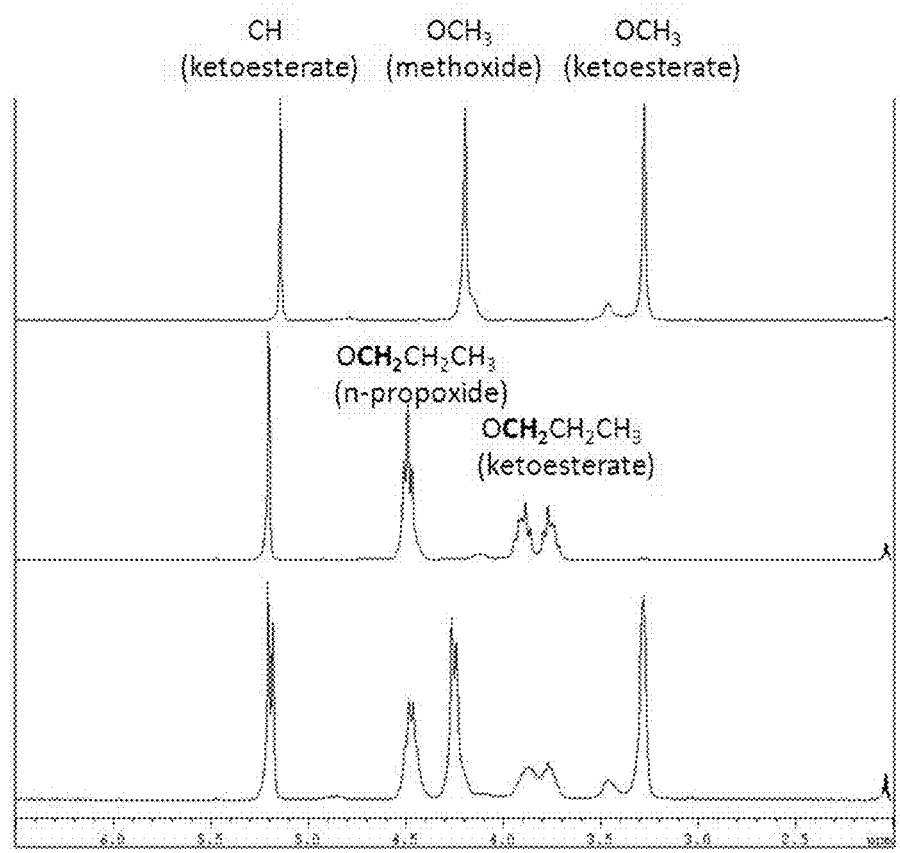
FIG. 5 shows $^1$H NMR spectra of $d^8$-toluene solutions of bis(methoxy)bis(methyl 4,4-dimethyl-3-oxopentanoato)titanium (top), bis(n-propoxy)bis(n-propyl 4,4-dimethyl-3-oxopentanoato)titanium (middle), and approximate 1:1 mixture of bis(methoxy)bis(methyl 4,4-dimethyl-3-oxopentanoato)

Inter-molecular exchange of alkoxy ligands in the above Formula B metal precursor complexes would result in even more complicated mixtures of the complexes having various combination of alkoxy and ketoesterate ligands, and thus different molecular weights. For example, FIG. 5 shows $^1$H NMR spectra of $d^8$-toluene solutions of: (a) bis(methoxy)bis (methyl 4,4-dimethyl-3-oxopentanoato)titanium, top graph, (b) bis(n-propoxy)bis(n-propyl 4,4-dimethyl-3-oxopentanoato)titanium, middle graph, and their (c) mixture, bottom graph. Presence of two methoxy signals in $^1$H NMR spectra of the mixture, lower graph, suggests inter-molecular ligand exchange of methoxy ligands between the two complexes, (a) and (b) and presence of mixed complexes (c) having both methoxy and n-propyl 4,4 dimethyl-3-oxopentanoato ligands, which are not present in the individual compounds (a) and (b).

Formula C

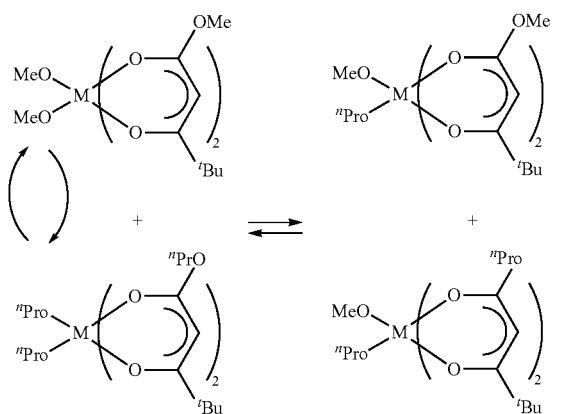

Figure 1:
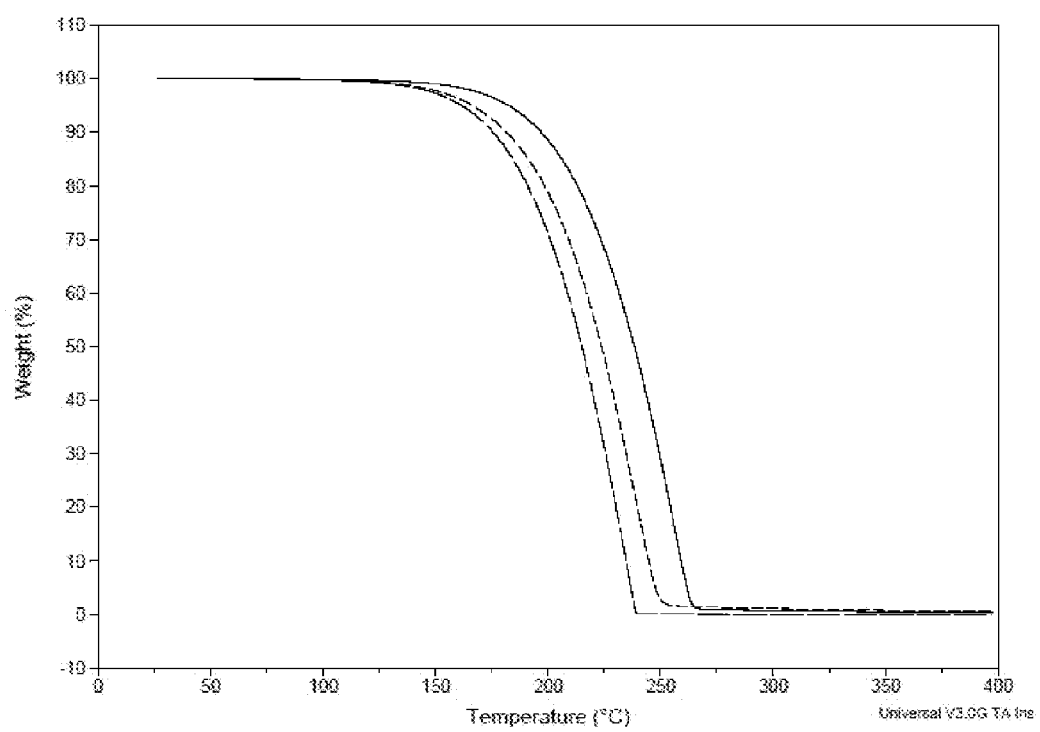
FIG. 1 is a graph of thermogravimetric analysis (TGA) for bis(methoxy)bis(methyl 4,4-dimethyl-3-oxopentanoato)titanium (long dashed line) having common alkoxy groups, a liquid material distilled from crude bis(n-propoxy)bis(methyl 4,4-dimethyl-3-oxopentanoato)titanium (shorter dashed line) having different alkoxy groups, and bis(n-propoxy)bis(n-propyl-4,4-dimethyl-3-oxopentanoato)titanium (solid line) having common but larger alkoxy groups, indicating that all precursors are volatile and have low residue. It also indicates that these three precursors have different volatility due to different combination of alkoxy ligands and ketoesterate ligands.
Figure 2:
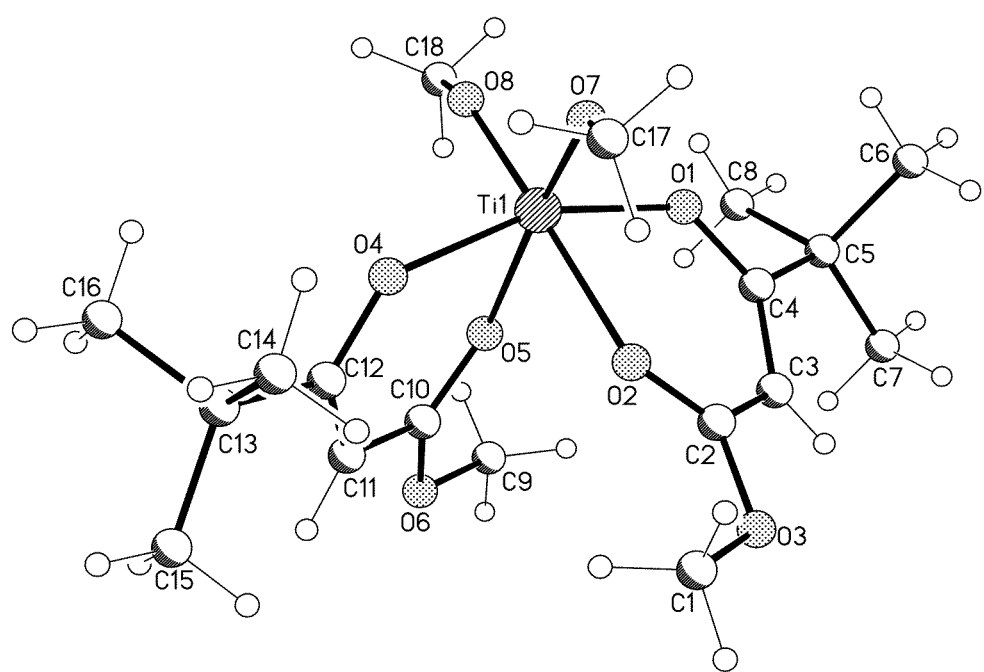
FIG. 2 is a schematic representation of a crystal structure of bis(methoxy)bis(methyl 4,4-dimethyl-3-oxopentanoato)titanium.

FIG. 1 demonstrates that Group 4 metal complexes having different combination of alkoxy and ketoesterate ligands have different volatility (boiling points).

Figure 4:
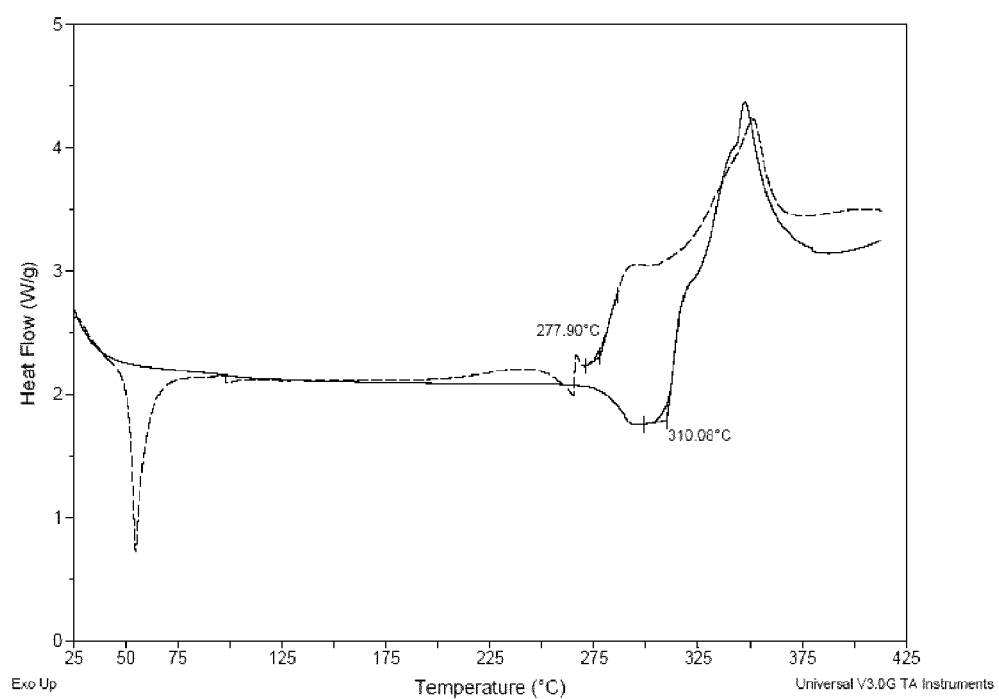
FIG. 4 is the comparison of differential scanning calorimetry (DSC) in high pressure sealed capsules at 10° C./min heating rate of bis(ethoxy)bis(ethyl 4,4-dimethyl-3-oxopentanoato)titanium (solid line) having common alkoxy groups and bis(ethoxy)bis(ethyl acetoacetato)titanium (dashed line) having common alkoxy groups. DSC data show that bis(ethoxy)bis(ethyl 4,4-dimethyl-3-oxopentanoato) titanium in which $R^2$ (ref. Formula A) is a branched alkyl (exotherm onset is 310° C.) has better thermal stability than bis(ethoxy)bis(ethyl acetoacetato)titanium in which $R^2$ (ref. Formula A) is a linear alkyl (exotherm onset is 278° C.).

Another advantage of the metal precursors of the present invention, in contrast to the other potential precursors containing ketoesterate ligands, is that the present invention's $R^2$ is selected from the group consisting of branched $C_{3-10}$ alkyls or aryls, preferably iso-propyl, iso-butyl, sec-butyl, tert-butyl or tert-amyl. Without being bound by any particular theory, it is believed that steric hindrance of the branched alkyl group, $R^2$, provides better thermal stability for the precursors of this invention. For example, FIG. 4 shows the comparison of differential scanning calorimetry (DSC) in high pressure sealed capsules at 10° C./min heating rate of bis(ethoxy)bis (ethyl 4,4-dimethyl-3-oxopentanoato)titanium (a precursor of this invention wherein $R^2$ is tert-butyl) and bis(ethoxy)bis (ethyl acetoacetato)titanium (wherein $R^2$ is methyl). DSC data show much better thermal stability of the precursor of this invention, where $R^2$ is branched (exotherm onset is 310° C.) compare to bis(ethoxy)bis(ethyl acetoacetato)titanium, wherein $R^2$ is a linear alkyl (exotherm onset is 278° C.).

In one embodiment of this invention a family of Group 4 metal precursors is represented by the formula: $M(OR^1)_2$ $(^tBuC(O)CHC(O)OR^1)_2$, also depicted in 2-dimensions as:

Formula D

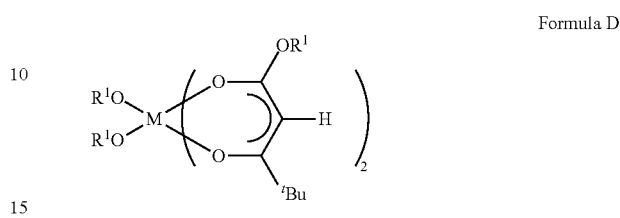

wherein M is a Group 4 metal selected from the group consisting of Ti, Zr, and Hf; wherein $R^1$ is selected from the group consisting of a linear or branched $C_{1-10}$ alkyl and a $C_{6-12}$ aryl, preferably methyl, ethyl, and n-propyl.

In yet another embodiment of this invention, a family of Group 4 metal precursors is represented by the formula: $Ti(OR^1)_2(^tBuC(O)CHC(O)OR^1)_2$ also depicted in 2-dimensions as:

Formula E

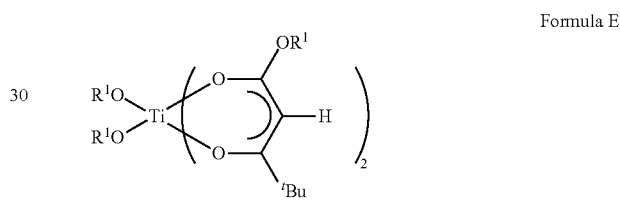

wherein $R^1$ is selected from the group consisting of methyl, ethyl, and propyl.

In one particular embodiment, the Group 4 metal precursor exhibits at least one of the following properties: low molecular weight (e.g., 500 m.u. or below), low viscosity (600 cP and below), low melting point (e.g., 60° C. or below), and high vapor pressure (e.g., 0.5 torr or greater).

Also described herein is a method for making a Group 4 metal containing film, such as: metal containing oxide film; metal containing nitride film, metal containing oxynitride film, metal containing silicate film, multi-component metal oxide film, and any combination or laminate thereof, which may be used, for example, in fabricating semiconductor devices.

In one embodiment, the method disclosed herein provides a Group 4 metal or multi-component metal oxide film that has a dielectric constant substantially higher than that of any of: conventional thermal silicon oxide, silicon nitride, or zirconium/hafnium oxide dielectric.

The method disclosed herein deposits the Group 4 metal containing films using atomic layer deposition (ALD) or chemical vapor deposition (CVD) processes. Examples of suitable deposition processes for the method disclosed herein include, but are not limited to, cyclic CVD (CCVD), MOCVD (Metal Organic CVD), thermal chemical vapor deposition, plasma enhanced chemical vapor deposition (PECVD), high density PECVD, photon assisted CVD, plasma-photon assisted (PPECVD), cryogenic chemical vapor deposition, chemical assisted vapor deposition, hot-filament chemical vapor deposition, CVD of a liquid polymer precursor, deposition from supercritical fluids, and low energy CVD (LECVD). In certain embodiments, the metal containing films are deposited via plasma enhanced ALD (PEALD) or plasma enhanced cyclic CVD (PECCVD) process. In these embodiments, the deposition temperature may be relatively lower, or may range from 200° C. to 400° C., and may allow for a wider process window to control the specifications of film properties required in end-use applications. Exemplary deposition temperatures for the PEALD or PECCVD deposition include ranges having any one of the following endpoints: 200, 225, 250, 275, 300, 325, 350, 375, and 400° C.

In one embodiment of the method disclosed herein, a Group 4 metal silicate or metal silicon oxynitride film is formed onto at least one surface of a substrate using a Group 4 metal precursor of Formula A, a silicon-containing precursor, an oxygen source, and optionally a nitrogen source. Although metal-containing and silicon-containing precursors typically react in either liquid form or gas phase, thereby preventing film formation, the method disclosed herein avoids pre-reaction of the metal containing and silicon-containing precursors by using ALD or CCVD methods that separate the precursors prior to and/or during the introduction to the reactor. In this connection, deposition techniques, such as an ALD or CCVD processes, are used to deposit the metal-containing film. For example, in certain embodiments, an ALD process is used to deposit the metal-containing film. In a typical ALD process, the film is deposited by exposing the substrate surface alternatively to the metal precursor or the silicon-containing precursors. Film growth proceeds by self-limiting control of surface reaction, the pulse length of each precursor, and the deposition temperature. However, once the surface of the substrate is saturated, the film growth ceases. In yet another embodiment, the metal-containing film may be deposited using a CCVD process. In this embodiment, the CCVD process may be performed using a higher temperature range than the ALD window, or from 350° C. to 600° C. Exemplary deposition temperatures for the CCVD deposition include ranges having any one of the following endpoints (provided in degrees Celsius): 200, 225, 250, 275, 300, 325, 350, 375, 400, 425, 450, 475, 500, 525, 550, 575, and 600° C.

Without being bound by any theory, it is believed that precursors of this invention can be particularly useful for ALD of metal containing films. Precursors of this invention may have an ALD operating thermal window greater than 350° C., and ALD growth rates higher than 0.3 Å/cycle, preferably greater than 0.5 Å/cycle.

In certain embodiments, the method disclosed herein forms the metal oxide films using group 4 metal precursors and an oxygen source. The oxygen source can be selected from the group consisting of oxygen, plasma oxygen, nitrous oxide, ozone, water, plasma water, and mixture thereof.

As mentioned previously, the method disclosed herein forms the metal containing films using at least one metal precursor, such as the Group 4 metal containing precursors described herein, optionally at least one silicon-containing precursor, optionally an oxygen source, optionally an additional metal-containing or other metal-containing precursor, optionally a reducing agent, and optionally a nitrogen source. Although the precursors and sources used herein may sometimes be described as "gaseous", it is understood that the precursors can be either liquid or solid, which are transported with or without an inert gas into the reactor via direct vaporization, bubbling or sublimation. In some case, the vaporized precursors can pass through a plasma generator.

In certain embodiments, other metal containing precursors can be used in addition to the Group 4 metal precursors described herein. Metals commonly used in semiconductor fabrication, that can be used as the metal component for a metal amide include: titanium, tantalum, tungsten, hafnium, zirconium, cerium, zinc, thorium, bismuth, lanthanum, strontium, barium, lead, and combinations thereof. Examples of other metal containing precursors, that may be used with the method disclosed herein include, but are not limited to: tetrakis(dimethylamino)zirconium (TDMAZ), tetrakis(diethylamino)zirconium (TDEAZ), tetrakis(ethylmethylamino)zirconium (TEMAZ), tetrakis(dimethylamino)hafnium (TDMAH), tetrakis(diethylamino)hafnium (TDEAH), and tetrakis(ethylmethylamino)hafnium (TEMAH), tetrakis(dimethylamino)titanium (TDMAT), tetrakis(diethylamino)titanium (TDEAT), tetrakis(ethylmethylamino)titanium (TEMAT), tert-butylimino tri(diethylamino)tantalum (TBTDET), tert-butylimino tri(dimethylamino)tantalum (TBTDMT), tert-butylimino tri(ethylmethylamino)tantalum (TBTEMT), ethylimino tri(diethylamino)tantalum (EITDET), ethylimino tri(dimethylamino)tantalum (EITDMT), ethylimino tri(ethylmethylamino)tantalum (EITEMT), tert-amylimino tri(dimethylamino)tantalum (TAIMAT), tert-amylimino tri(diethylamino)tantalum, pentakis(dimethylamino)tantalum, tert-amylimino tri(ethylmethylamino) tantalum, bis(tert-butylimino)bis(dimethylamino)tungsten (BTBMW), bis(tert-butylimino)bis(diethylamino)tungsten, bis(tert-butylimino)bis(ethylmethylamino)tungsten, bis(2,2,6,6-tetramethyl-3,5-heptanedionato)strontium, bis(2,2,6,6-tetramethyl-3,5-heptanedionato)barium, $M(R_nC_5H_{5-n})_2$, wherein n=1-5 and R is selected from linear or branched $C_{1-6}$ alkyls; $M(R_nC_4NH_{4-n})_2$, wherein n=2-4, R is selected from linear or branched $C_{1-6}$ alkyls, and $M(R_nN_2H_{3-n})_2$, where n=2-3, R is selected from linear or branched $C_{1-6}$ alkyls, and combinations thereof.

In one embodiment, the metal containing precursors, that can be used in addition to the Group 4 metal precursors described herein to provide a metal-containing film, are polydentate β-ketoiminates which are described, for example, in Applicants' co-pending application US2007/0248754A1, U.S. Ser. No. 11/945,678 filed on Nov. 27, 2007, Applicants' co-pending U.S. application Ser. No. 12/266,806 which was filed on Nov. 11, 2008 Applicants' U.S. Pat. No. 7,691,984, U.S. Pat. No. 7,723,493, all of which are incorporated herein by reference in their entirety.

In certain embodiments, the polydentate β-ketoiminates may incorporate an alkoxy group in the imino group. The polydentate β-ketoiminates are selected from the group represented by the following Formula F and G:

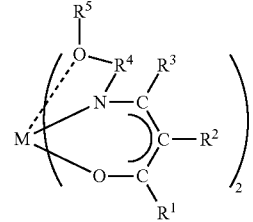

Formula F wherein M is a Group 2 metal such as, for example, magnesium, calcium, strontium, and barium. Preferably, M is strontium or barium. The organo groups (i.e., the $R^{1-5}$ groups) employed in the complexes of Formula F may include a variety of organo groups and they may be linear or branched. In preferred embodiments, $R^1$ is selected from the group consisting of: a $C_{1-10}$ alkyl, a $C_{1-10}$ alkoxyalkyl, a $C_{1-10}$ alkoxy, a $C_{1-10}$ fluoroalkyl, a $C_{1-10}$ cycloaliphatic, and a $C_{6-10}$ aryl. As used herein, the group "alkoxyalkyl" refers to an ether-like moiety that includes a C—O—C fragment. Examples include —CH$_2$CH$_2$—O—CH$_2$CH$_2$—O—CH$_3$ and —CH$_2$CH$_2$—O—CH$_2$—O—CH$_3$. Preferably, R$^1$ is a bulky alkyl group containing 4 to 6 carbon atoms, such as, for example; a tert-butyl group, a sec-butyl, and a tert-pentyl group. The most preferred R$^1$ group is tert-butyl or tert-pentyl. Preferably, R$^2$ is selected from the group consisting of: hydrogen, a C$_{1-10}$ alkyl, a C$_{1-10}$ alkoxyalkyl, a C$_{1-10}$ alkoxy, a C$_{3-10}$ cycloaliphatic, and a C$_{6-10}$ aryl. More preferably, R$^2$ is hydrogen, or a C$_{1-2}$ alkyl. Preferably, R$^3$ is selected from the group consisting of: a C$_{1-10}$ alkyl, a C$_{1-10}$ alkoxyalkyl, a C$_{1-10}$ alkoxy, a C$_{3-10}$ cycloaliphatic, and a C$_{6-10}$ aryl. More preferably, R$^3$ is a C$_{1-2}$ alkyl. Preferably, R$^4$ is a C$_{1-6}$ linear or branched alkylene and, more preferably, R$^4$ contains a branched alkylene bridge containing C$_{3-4}$ and having at least one chiral center carbon atom. Without intending to be bound by a particular theory, it is believed that the chiral center in the ligand plays a role in lowering the melting point, as well as increasing the thermal stability of the complex. Preferably, R$^5$ is selected from the group consisting of: a C$_{1-10}$ alkyl, a C$_{1-10}$ fluoroalkyl, a C$_{3-10}$ cycloaliphatic, and a C$_{6-10}$ aryl. More preferably, R$^5$ is a C$_{1-2}$ alkyl.

Specific examples of these metal containing complexes are represented by the following Formula G:

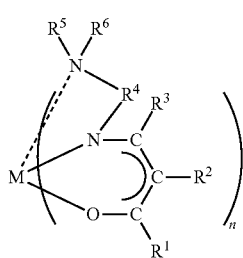

Formula G wherein M is a metal group having a valence of from 2 to 5 wherein R$^1$ is selected from the group consisting of alkyl, alkoxyalkyl, fluoroalkyl, cycloaliphatic, and aryl, having C$_{1-10}$ carbon atoms; R$^2$ is selected from the group consisting of hydrogen, C$_{1-10}$ alkyl, C$_{1-10}$ alkoxy, C$_{4-10}$ cycloaliphatic, and C$_{6-12}$ aryl; R$^3$ is selected from the group consisting of C$_{1-10}$ alkyl, C$_{1-10}$ alkoxyalkyl, C$_{1-10}$ fluoroalkyl, C$_{4-10}$ cycloaliphatic, and C$_{6-12}$ aryl; R$^4$ is a C$_{3-10}$ linear or branched alkyl bridge, preferably R$^4$ is having at least one chiral carbon atom; R$^{5-6}$ are individually selected from the group consisting of C$_{1-10}$ alkyl, C$_{1-10}$ fluoroalkyl, C$_{4-10}$ cycloaliphatic, C$_{6-12}$ aryl, and heterocyclic containing either oxygen, or nitrogen atoms; and n is an integer equal to the valence of the metal M.

In one embodiment metal precursors of this invention can be used in addition to at least one metal-ligand complex, wherein one or more ligands of the metal-ligand complex are selected from the group consisting of β-diketonates, β-diketoesterate, β-ketoiminates, β-diiminates, alkyls, carbonyl, alkyl carbonyl, cyclopentadienyls, pyrrolyl, imidazolyl, amidinate, alkoxy, and mixtures thereof, wherein the ligand can be monodentate, bidentate and multidentate, and the metal of the metal-ligand complex is selected from Group 2 to 16 elements of the Periodic Table of the Elements. Examples of these complexes comprise: bis(2,2-dimethyl-5-(dimethylaminoethyl-imino)-3-hexanonato-N,O,N')strontium, bis(2,2-dimethyl-5-(1-dimethylamino-2-propylimino)-3-hexanonato-N,O,N')strontium, tetrakis(2,2,6,6-tetramethyl-3,5-heptanedionato)cerium (IV), tris(2,2,6,6-tetramethyl-3,5-heptanedionato)lanthanum, Sr[($^t$Bu)$_3$Cp]$_2$, Sr[($^i$Pr)$_3$Cp]$_2$, Sr[($^n$PrMe$_4$Cp]$_2$, Ba[($^t$Bu)$_3$Cp]$_2$, LaCp$_3$, La(MeCp)$_3$, La(EtCp)$_3$, La($^i$PrCp)$_3$, zirconium tert-butoxide, strontium bis(2-tert-butyl-4,5-di-tert-amylimidazolate), barium bis(2-tert-butyl-4,5-di-tert-amylimidazolate), barium bis(2,5-di-tert-butyl-pyrrolyl), where "Bu" is butyl, "Cp" is cyclopentadienyl, "Me" is methyl, "Et" is ethyl, and "Pr" is propyl.

In one embodiment, metal precursors of this invention can be used for deposition of titanium oxide, doped titanium oxide, doped zirconium oxide, strontium titanate (STO) and barium strontium titanate (BST).

In embodiments wherein the metal film deposited is a metal silicate, the deposition process further involves the introduction of at least one silicon-containing precursor. Examples of suitable silicon-containing precursors, include: a monoalkylaminosilane precursor, a hydrazinosilane precursor, or combinations thereof.

In certain embodiments, the silicon-containing precursor comprises a monoalkylaminosilane precursor having at least one N—H fragment and at least one Si—H fragment. Suitable monoalkylaminosilane precursors containing both the N—H fragment and the Si—H fragment include, for example: bis(tert-butylamino)silane (BTBAS), tris(tert-butylamino)silane, bis(iso-propylamino)silane, tris(iso-propylamino)silane, and mixtures thereof. In one embodiment, the monoalkylaminosilane precursor has the formula (R$^7$NH)$_n$SiR$^8_m$H$_{4-(n+m)}$ wherein R$^7$ and R$^8$ are the same or different and independently selected from the group consisting of C$_{1-10}$ alkyl, vinyl allyl, phenyl, C$_{4-10}$ cyclic alkyl, C$_{1-10}$ fluoroalkyl, and C$_{1-10}$ silylalkyl and wherein n is a number ranging from 1 to 3, m is a number ranging from 0 to 2, and the sum of "n+m" is a number that is less than or equal to 3. In another embodiment, the silicon-containing precursor comprises a hydrazinosilane having the formula (R$^9_2$N—NH)$_x$SiR$^{10}_y$H$_{4-(x+y)}$ wherein R$^9$ and R$^{10}$ are same or different and independently selected from the group consisting of C$_{1-10}$ alkyl, vinyl, allyl, phenyl, C$_{4-10}$ cyclic alkyl, C$_{1-10}$ fluoroalkyl, C$_{1-10}$ silylalkyls and wherein x is a number ranging from 1 to 2, y is a number ranging from 0 to 2, and the sum of "x+y" is a number that is less than or equal to 3. Examples of suitable hydrazinosilane precursors include, but are not limited to: bis(1,1-dimethylhydrazino)-silane, tris(1,1-dimethylhydrazino)silane, bis(1,1-dimethylhydrazino)ethylsilane, bis(1,1-dimethylhydrazino)isopropylsilane, bis(1,1-dimethylhydrazino)vinylsilane, and mixtures thereof.

Depending upon the deposition method, in certain embodiments, the silicon-containing precursor may be introduced into the reactor at a predetermined molar volume, or from about 0.1 to about 1000 micromoles. In this or other embodiments, the silicon-containing precursor may be introduced into the reactor for a predetermined time period, or from about 0.001 to about 500 seconds. The silicon-containing precursors react with the metal hydroxyl groups formed by the reaction of the metal amide with the oxygen source and become chemically adsorbed onto the surface of the substrate, which results in the formation of a silicon oxide or a silicon oxynitride via metal-oxygen-silicon and metal-oxygen-nitrogen-silicon linkages, thus providing the metal silicate or the metal silicon oxynitride film.

As previously mentioned, some of the films deposited using the methods described herein (e.g., metal silicate or the metal silicon oxynitride films) may be formed in the presence of oxygen. An oxygen source may be introduced into the reactor in the form of at least one oxygen source and/or may be present incidentally in the other precursors used in the deposition process. Suitable oxygen source gases may include, for example: water (H$_2$O) (e.g., deionized water, purifier water, and/or distilled water), oxygen (O$_2$), oxygen plasma, ozone ($O_3$), NO, $NO_2$, carbon monoxide (CO), carbon dioxide ($CO_2$) and combinations thereof. In certain embodiments, the oxygen source comprises an oxygen source gas, that is introduced into the reactor at a flow rate ranging from about 1 to about 2000 square cubic centimeters (sccm) or from about 1 to about 1000 sccm. The oxygen source can be introduced for a time that ranges from about 0.1 to about 100 seconds. In one particular embodiment, the oxygen source comprises water having a temperature of 10° C. or greater. In this or other embodiments wherein the film is deposited by an ALD process, the precursor pulse can have a pulse duration that is greater than 0.01 seconds, and the oxidant pulse duration can have a pulse duration that is greater than 0.01 seconds, while the water pulse duration can have a pulse duration that is greater than 0.01 seconds. The deposition methods disclosed herein may involve one or more purge gases. The purge gas, which is used to purge away unconsumed reactants and/or reaction byproducts, is an inert gas that does not react with the precursors and may preferably be selected from: Ar, $N_2$, He, $H_2$ and mixture thereof. In certain embodiments, a purge gas, such as Ar, is supplied into the reactor at a flow rate ranging from about 10 to about 2000 sccm for about 0.1 to 1000 seconds, thereby purging the unreacted material and any by-product that remain in the reactor.

In certain embodiments, such as, for example, for those embodiments where a metal silicon oxynitride film is deposited, an additional gas, such as a nitrogen source gas, may be introduced into the reactor. Examples of nitrogen source gases may include, for example: NO, $NO_2$, ammonia, hydrazine, monoalkylhydrazine, dialkylhydrazine, and combinations thereof.

In one embodiment of the method described herein, the temperature of the substrate in the reactor, i.e., a deposition chamber, is about 600° C. or below or about 500° C. or below or from 250 to 400° C. In this or other embodiments, the pressure may range from about 0.1 Torr to about 100 Torr or from about 0.1 Torr to about 5 Torr.

The respective step of supplying the precursors, the oxygen source, and/or other precursors or source gases may be performed by changing the time for supplying them to change the stoichiometric composition of the resulting metal silicate, metal silicon oxynitride film, or other metal-containing film.

Energy is applied to the at least one of the precursor, oxygen source gas, reducing agent, or combination thereof to induce reaction and to form the metal-containing film on the substrate. Such energy can be provided by, but not limited to, thermal, plasma, pulsed plasma, helicon plasma, high density plasma, inductively coupled plasma, X-ray, e-beam, photon, and remote plasma methods. In certain embodiments, a secondary radio frequency (RF) frequency source can be used to modify the plasma characteristics at the substrate surface. In embodiments wherein the deposition involves plasma, the plasma-generated process may comprise a direct plasma-generated process in which plasma is directly generated in the reactor, or alternatively a remote plasma-generated process in which plasma is generated outside of the reactor and supplied into the reactor.

In yet another embodiment of the method disclosed herein, the Group 4 metal containing film is formed using a vapor deposition method that comprises the steps of: (a) introducing a Group 4 metal precursor in a vapor state into a reaction chamber and chemisorbing the Group 4 metal precursor onto a substrate which is heated; (b) purging away the unreacted Group 4 metal precursor; (c) introducing an oxygen source onto the heated substrate to react with the sorbed Group 4 metal precursor; and (d) purging away the unreacted oxygen source. The above steps define one cycle for the method described herein; and the cycle can be repeated until the desired thickness of a metal-containing film is obtained. In this or other embodiments, it is understood that the steps of the methods described herein may be performed in a variety of orders, may be performed sequentially or concurrently (e.g., during at least a portion of another step), and any combination thereof. The respective step of supplying the precursors and the oxygen source gases may be performed by varying the duration of the time for supplying them to change the stoichiometric composition of the resulting metal oxide film. For multicomponent metal oxide films, a strontium-containing precursor, a barium-containing precursor or both precursors can be alternately introduced in step a into the reactor chamber.

The Group 4 metal precursor and/or other metal containing precursors may be delivered to the reaction chamber, such as a CVD or ALD reactor, in a variety of ways. In one embodiment, a liquid delivery system may be utilized. In an alternative embodiment, a combined liquid delivery and flash vaporization process unit may be employed, such as, for example, the turbo vaporizer manufactured by MSP Corporation of Shoreview, Minn., USA, to enable low volatility materials to be volumetrically delivered, leading to reproducible transport and deposition without thermal decomposition of the precursor. Both of these considerations of reproducible transport and deposition without thermal decomposition are essential for providing a commercially acceptable copper CVD or ALD process.

In one embodiment of the method described herein, a cyclic deposition process such as CCVD, ALD, or PEALD may be employed, wherein a Group 4 metal precursor or its solution and an oxygen source, such as; for example, ozone, oxygen plasma or water plasma, are employed. The gas lines connecting from the precursor canisters to the reaction chamber are heated to one or more temperatures ranging from about 150° C. to about 200° C. depending upon the process requirements, and the container of the Group 4 metal precursor is kept at one or more temperatures ranging from about 100° C. to about 190° C. for bubbling, wherein the solution comprising the Group 4 metal precursor is injected into a vaporizer kept at one or more temperatures ranging from about 150° C. to about 180° C. for direct liquid injection. A flow of 100 sccm of argon gas may be employed as a carrier gas to help deliver the vapor of the Group 4 metal precursor to the reaction chamber during the precursor pulsing. The reaction chamber process pressure is about 1 Torr. In a typical ALD or CCVD process, the substrate, such as silicon oxide or metal nitride, are heated on a heater stage in a reaction chamber that is exposed to the Group 4 metal precursor initially to allow the complex to chemically adsorb onto the surface of the substrate. An inert gas, such as argon gas, purges away unadsorbed excess complex from the process chamber. After sufficient Ar purging, an oxygen source is introduced into reaction chamber to react with the absorbed surface followed by another inert gas purge to remove reaction by-products from the chamber. The process cycle can be repeated to achieve the desired film thickness.

In liquid delivery formulations, the precursors described herein may be delivered in neat liquid form, or alternatively, may be employed in solvent formulations or compositions comprising same. Thus, in certain embodiments the precursor formulations may include solvent component(s) of suitable character as may be desirable and advantageous in a given end use application to form a film on a substrate. The solvent employed in solubilizing the precursor for use in a deposition process may comprise any compatible solvent or their mixture, including; aliphatic hydrocarbons (e.g., pentane, hexane, heptane, octane, decane, dodecane, ethylcyclohexane, propylcyclohexane), aromatic hydrocarbons (e.g., benzene, toluene, ethylbenzene, xylene, mesitylene, ethyl toluene and other alkyl substituted aromatic solvents), ethers, esters, nitriles, alcohols, amines (e.g., triethylamine, tert-butylamine), imines and carbodiimides (e.g., N,N'-diisopropylcarbodiimide), ketones, aldehydes, amidines, guanadines, isoureas, and the like. Further examples of suitable solvents are selected from the group consisting of glyme solvents having from 1 to 20 ethoxy —$(C_2H_4O)$— repeat units (e.g. dimethoxyethane, 1,2-diethoxyethane and diglyme); organic ethers selected from the group consisting of propylene glycol groups (e.g. dipropylene glycol dimethyl ether); $C_2$-$C_{12}$ alkanols; organic ethers selected from the group consisting of dialkyl ethers comprising $C_1$-$C_6$ alkyl moieties, $C_4$-$C_8$ cyclic ethers (e.g. tetrahydrofuran and dioxane); $C_{12}$-$C_{60}$ crown $O_4$-$O_{20}$ ethers wherein the prefixed $C_i$ range is the number i of carbon atoms in the ether compound and the suffixed $O_i$ range is the number i of oxygen atoms in the ether compound; $C_6$-$C_{12}$ aliphatic hydrocarbons; $C_6$-$C_{18}$ aromatic hydrocarbons; organic esters; organic amines, polyamines, aminoethers and organic amides. Another class of solvents that offers advantages is the organic amide class of the form RCONR'R" wherein R and R' are alkyl having from 1-10 carbon atoms and they can be connected to form a cyclic group $(CH_2)_n$, wherein n is from 4-6, preferably 5, and R" is selected from alkyl having from 1 to 4 carbon atoms and cycloalkyl. N-methyl- or N-ethyl- or N-cyclohexyl-2-pyrrolidinones, N,N-Diethylacetamide, and N,N-Diethylformamide are examples.

The utility of specific solvent compositions for particular precursors may be readily empirically determined, to select an appropriate single component or multiple component solvent medium for the liquid delivery vaporization and transport of the specific copper precursor that is employed.

In another embodiment, a direct liquid delivery method can be employed by dissolving the Group 4 metal precursor in a suitable solvent or a solvent mixture to prepare a solution with a molar concentration from 0.01 to 2 M, depending the solvent or mixed-solvents employed. The solvent employed herein may comprise any compatible solvents or their mixture including, but not limited to, aliphatic hydrocarbons, aromatic hydrocarbons, linear or cyclic ethers, esters, nitriles, alcohols, amines, polyamines, aminoethers and organic amides, preferably a solvent with a high boiling point, such as octane, ethylcyclohexane, decane, dodecane, xylene, mesitylene and dipropylene glycol dimethyl ether.

The method described herein also includes a cyclic deposition process for the formation of ternary metal oxide films, wherein a plurality of precursors are sequentially introduced into a deposition chamber, vaporized and deposited on a substrate under conditions for forming a said ternary metal oxide film.

In one particular embodiment, the resultant metal oxide films can be exposed to a post-deposition treatment, such as a plasma treatment to densify the film.

As mentioned previously, the method described herein may be used to deposit a metal-containing film on at least a portion of a substrate. Examples of suitable substrates include, but are not limited to, semiconductor materials, such as strontium titanate, barium strontium titanate, yttrium oxide doped with titanium, lanthanum oxide doped with titanium, and other lanthanide oxides doped with titanium.

The following examples illustrate the method for preparing a Group 4 metal precursor described herein and are not intended to limit it in any way.

Comparative Example 1

Synthesis of bis(iso-propoxy)bis(methyl 4,4-dimethyl-3-oxopentanoato)titanium

To 2.00 g (7.04 mmol) Ti(IV) isopropoxide was slowly added 2.25 g (14.24 mmol) methyl 4,4-dimethyl-3-oxopentanoate (MDOP) at 25° C. The resulting yellow viscous solution was heated to 43° C. due to exothermic reaction and then agitated at 25° C. for 2 hours. Removal of all volatiles generated a white glassy solid. The solid was re-dissolved in 4 ml of hexanes, the mixture was agitated and hexanes was removed under vacuum to obtain white crystalline solid, 2.65 g (78% yield). Melting point of the product was 68° C. 2.12 g of solid was purified by sublimation at 85° C. under vacuum (0.2 torr). 2.03 g of sublimed product was collected (96% sublimation yield).

$^1$H-NMR confirms no uncoordinated methyl 4,4-dimethyl-3-oxopentanoate and shows the desired ratio of $^i$PrO to MDOP coordinated to Ti being two $^i$PrO's to two MDOP ligands.

$^1$H-NMR (500 MHz, THF) δ(ppm): 5.12 (CH, MDOP), 4.69 (CH, O-iPr), 3.55 and 3.80 (OCH$_3$,MDOP), 1.40 [(CH$_3$)$_2$], 1.05 and 1.20 [C(CH$_3$)$_3$ and C(CH$_3$)$_2$].

A neat sample of this material was heated at 200° C. for one hour in a sealed NMR tube under nitrogen atmosphere and the material quickly turned dark orange indicating some decomposition. GC-MS of the heated sample dissolved in acetone showed presence of both ketoesters: methyl 4,4-dimethyl-3-oxopentanoate (57.4%) and iso-propyl 4,4-dimethyl-3-oxopentanoate (42.6%, product of transesterification reaction). GC-MS of the non-heated sample dissolved in acetone showed the presence of only methyl 4,4-dimethyl-3-oxopentanoate. $^1$H NMR spectrum of the heated material dissolved in d$_8$-toluene also confirmed the presence of various complexes containing both ketoesterate ligands and methoxy ligands (δ(ppm) 4.25 and 4.30), which were not present in the material before thermal treatment.

Comparative Example 2

Synthesis of bis(ethoxy)bis(methyl 4,4-dimethyl-3-oxopentanoato) titanium

To a solution of 2.0 g (8.78 mmol) Ti(IV) ethoxide in 6 milliliters (mL) of hexane was added 2.75 g (17.4 mmol) of MDOP. The resulting yellow solution was stirred for 16 hours at room temperature (RT), and all volatiles were removed under vacuum. 3.0 g of orange liquid (88% crude yield) was purified by distillation at 180° C. under vacuum (0.2 torr) to obtain 2.71 g of light yellow viscous liquid (79.9% purified yield). $^1$H-NMR of distilled product indicates presence of different ethoxy groups attributed to signals from ethoxide ligands and also from ethyl 4,4-dimethyl-3-oxopentanoato (EDOP) ligand likely formed by transesterification reaction. Gas chromatograph-Mass spectroscopy (GC-MS) of acetone solution of distilled product confirmed presence of a mixture of methyl 4,4-dimethyl-3-oxopentanoate and ethyl 4,4-dimethyl-3-oxopentanoate present at ~2/1 ratio.

$^1$H-NMR (500 MHz, C$_6$D$_6$) δ(ppm): 5.40 (CH, EDOP), 4.70 (OCH$_2$, ethoxy), 4.40 (OCH$_3$, ethoxy), 4.0 (OCH$_2$, EDOP), 3.40 and 3.65 (OCH$_3$, MDOP), 1.35 (CH$_3$, ethoxy), 1.15 and 1.26 (C(CH$_3$)$_3$, MDOP).

Comparative Example 3

Synthesis of bis(n-propoxy)bis(methyl 4,4-dimethyl-3-oxopentanoato) titanium To a solution of 15.1 g (53.1 mmol) Ti(IV) n-propoxide in 30 g of anhydrous hexanes at 5° C. was added 18.0 g (113.9 mmol) MDOP. The resulting solution was agitated for 16 hours at room temperature (RT) and then refluxed for two hours. All volatiles were removed under vacuum and orange viscous liquid was obtained (24.74 g, 96.6% crude yield). The material was distilled under vacuum at 190° C. to obtain 19.2 g of light yellow viscous liquid (75% purified yield). $^1$H-NMR of distilled product indicates presence of different n-propoxy groups attributed to signals from n-propoxide ligands and also from propyl 4,4-dimethyl-3-oxopentanoato ligand, likely formed by transesterification reaction. GC-MS of acetone solution of distilled product confirmed presence of a mixture of methyl 4,4-dimethyl-3-oxopentanoate and propyl 4,4-dimethyl-3-oxopentanoate present at ~1/1 ratio.

1H NMR of crude material containing >90% of bis(n-propoxy)bis(methyl 4,4-dimethyl-3-oxopentanoato) titanium (500 MHz, d$_8$-toluene δ(ppm): 5.20 (CH, MDOP), 4.47 (OCH$_2$, n-propoxy), 3.35 and 3.55 (OCH$_3$, MDOP), 1.57 (OCH$_2$, n-propoxy), 1.05 and 1.29 (C(CH$_3$)$_3$, MDOP), 0.92 (CH$_3$, n-propoxy).

$^1$H-NMR of the distilled material indicates it is a mixture of complexes containing both methyl 4,4-dimethyl-3-oxopentanoato and propyl 4,4-dimethyl-3-oxopentanoato ligands (500 MHz, d$_8$-toluene δ(ppm): 5.25 (CH, ketoesterates), 4.50 (OCH$_2$, n-propoxide), 4.3 (OCH$_3$, methoxy), 3.90 (OCH$_2$, ketoesterate), 3.35 and 3.55 (OCH$_3$, MDOP), 1.60 and 1.45 (OCH$_2$, n-propoxy), 1.05 and 1.20 (C(CH$_3$)$_3$, MDOP), 0.75 and 0.95 (CH$_3$, n-propoxy), confirming indeed the transesterification reaction occurred during distillation.

Comparative Example 4

Synthesis of bis(methoxy)bis(n-propyl 4,4-dimethyl-3-oxopentanoato) titanium To a slurry of 0.43 g (2.50 mmol) of Ti(IV) methoxide in 5 mL of hexanes was added 0.93 g (5.00 mmol) of n-propyl 4,4-dimethyl-3-oxopentanoate. The reaction mixture was agitated for 16 hours at RT and all Ti(IV) methoxide was dissolved. All volatiles were distilled under vacuum to obtain 1.0 g of light yellow liquid, ~83% crude yield. The material was not purified by high temperature vacuum distillation to avoid exchange of methoxide ligand with the ester group.

$^1$H-NMR (500 MHz, d$_8$-toluene δ(ppm): 5.27 (CH, ketoesterate), 4.54 (OCH$_3$, methoxy), 4.3 (OCH$_3$, methoxy), 3.90 (OCH$_2$, ketoesterate), 1.49 (OCH$_2$, ketoesterate), 1.05 and 1.20 (C(CH$_3$)$_3$, ketoesterate), 0.75 (CH$_3$, ketoesterate).

A neat sample of this material was heated at 200° C. for one hour in a sealed NMR tube under nitrogen atmosphere and significant changes were observed in its $^1$H NMR spectrum, as shown in FIG. 6. A mixture of complexes containing methoxide, n-propoxide ligands and also n-propyl 4,4-dimethyl-3-oxopentanoate and methyl 4,4-dimethyl-3-oxopentanoate ligands was present after thermal treatment.

Comparative Example 5

Synthesis of bis(ethoxy)bis(ethyl acetoacetato)titanium

To a solution of 5.76 g (25.24 mmol) of Ti(IV) ethoxide in 50 mL of tetrahydrofuran (THF) was added 6.57 g (50.47 mmol) of ethyl acetoacetate in 25 mL of THF. The reaction mixture was refluxed for 16 hours after which removal of volatiles yielded a waxy red-orange solid weighing 9.9 g. 3.41 g of crude material was purified by distillation at 130° C. under vacuum (125 mTorr) to obtain 2.90 g white solid (85% purified yield). The melting point was measured by the Differential scanning calorimetry (DSC) to be 52° C. $^1$H-NMR (500 MHz, C$_6$D$_6$) δ(ppm): 5.18 (CH), 4.73 (OCH$_2$CH$_3$), 3.95 and 3.92 (OCH$_2$CH$_3$, ketoester), 1.82 (CH$_3$, ketoester) 1.34 (OCH$_2$CH$_3$), 1.03 and 0.93 (OCH$_2$CH$_3$, ketoesterate).

A colorless plate-like crystal of bis(ethoxy)bis(ethyl acetoacetate)titanium was structurally characterized by X-ray single crystal analysis. The structure is confirmed to be a monomer, i.e. the titanium atom is coordinated with two ethoxy and two ethyl acetoacetato ligands in a distorted octahedral environment in which the two ethoxy groups are cis to each other, the two methyl groups are trans to each other, and the two esterate groups are cis to each other.

Comparative Example 6

Synthesis of bis(methoxy)bis(methyl acetoacetato)titanium

To a solution of 5.06 g (29.40 mmol) of Ti(IV) methoxide in 50 mL of THF was added 6.83 g (58.80 mmol) of methyl acetoacetate in 25 mL of THF. The reaction mixture was refluxed for 16 hours after which removal of volatiles yielded a pale yellow solid weighing 9.9 g. The crude material was extracted with 200 mL of hexanes and filtered. Removal of hexanes from the filtrate gave a yellow solid weighing 4.77 g (48% yield).

$^1$H-NMR (500 MHz, C$_6$D$_6$) δ(ppm): 5.14 (CH), 4.40 (OCH$_3$), 3.27 (OCH$_3$, ketoesterate), 1.80 (CH$_3$, ketoesterate).

A pale yellow block-like crystal of bis(methoxy)bis(methyl acetoacetate)titanium was structurally characterized by X-ray single crystal analysis. The structure is confirmed to be a monomer, i.e. the titanium atom is coordinated with two methoxy and two methyl acetoacetato ligands in a distorted octahedral environment in which the two methoxy groups are cis to each other position, the two methyl groups are trans to each other, and the two esterate groups are cis to each other.

Example 7

Synthesis of bis(methoxy)bis(methyl 4,4-dimethyl-3-oxopentanoato)titanium

To a suspension of 30.41 g (176.76 mmol) of Ti(IV) methoxide in 175 mL of THF was added 55.92 g (353.52 mmol) of methyl 4,4-dimethyl-3-oxopentanoate. The resulting reaction mixture was heated to reflux for 16 hours after which volatiles were removed. A beige milky oil was isolated and extracted with 150 mL of hexanes. It was then filtered through celite and removal of all volatiles yielded a viscous amber oil weighing 76.05 g. The oil was taken up in 100 mL of hexanes, and 65.70 g of pale yellow solid was precipitated out at −78° C. with a yield of 88%.

The melting point was measured by the Differential scanning calorimetry (DSC) at 10 C/min heating rate to be 51° C.

DSC at 10 C/min in a pressurized pan shows no thermal effects due to decomposition up to at least ~270° C. TGA analysis shows less than 0.2 wt. % residue, implying that it can be used as a suitable precursor in a vapor deposition process.

$^1$H-NMR (500 MHz, $C_6D_6$) δ(ppm): 5.36 (CH), 4.39 ($OCH_3$, methoxy), 3.29 ($OCH_3$,ketoesterate), 1.19 [$C(CH_3)_3$].

A colorless plate-like crystal of bis(methoxy)bis(methyl 4,4-dimethyl-3-oxopentanoato)titanium was structurally characterized by X-ray single crystal analysis. The structure shows the titanium atom is coordinated with two methoxy and two methyl 4,4-dimethyl-3-oxopentanoato ligands in a distorted octahedral environment as the two methoxy groups are cis to each other position, the two tert-butyl ($^t$Bu) groups are trans to each other, and the two esterate groups are cis to each other.

Example 8

Synthesis of bis(ethoxy)bis(ethyl 4,4-dimethyl-3-oxopentanoato) titanium

To a solution of 186.53 g (817.58 mmol) of Ti(IV) ethoxide in 300 mL of THF at room temperature was added 281.61 g (1635.15 mmol) of ethyl 4,4-dimethyl-3-oxopentanoate in 300 mL of THF via canula. Resulting red orange solution was refluxed for 16 hours. Removal of volatiles yielded a viscous orange liquid that was purified by distillation at 150° C. under vacuum (0.10 torr) to obtain 370.47 g of yellow viscous liquid. The yield is 93%.

DSC at 10 C/min in a pressurized pan shows no thermal effects due to decomposition up to ~270° C. TGA analysis shows that it leaves almost no residue, implying that it can be used as a suitable precursor in a vapor deposition process.

$^1$H-NMR (500 MHz, $C_6D_6$) δ(ppm): 5.37 (CH), 4.70 ($OCH_2CH_3$), 3.97 and 3.92 ($OCH_2CH_3$, ketoesterate), 1.34 ($OCH_2CH_3$), 1.23 and 1.10 [$C(CH_3)_3$], 1.03 and 0.96 ($OCH_2CH_3$, ketoesterate).

Example 9

Synthesis of bis(n-propoxy)bis(n-propyl 4,4-dimethyl-3-oxopentanoato) titanium

To a solution of 0.76 g (2.67 mmol) of Ti(IV) n-propoxide in 1 g of hexane was added 1.00 g (5.38 mmol) of n-propyl 4,4-dimethyl-3-oxopentanoate. The reaction mixture was agitated for one hour at RT and then for 30 minutes at 60° C. All volatiles were removed under vacuum to obtain 1.1 g of colorless liquid, ~69% isolated yield. The material was purified by vacuum distillation (0.2 torr) at 180° C. (pot temperature) and clear colorless liquid was collected. No changes in $^1$H NMR spectra of the materials before and after high temperature vacuum distillation were observed, indicating good thermal and compositional stability of this complex.

$^1$H-NMR (500 MHz, $d_8$-toluene δ(ppm): 5.17 (CH, ketoesterate), 4.45 ($OCH_2$, n-propoxide), 3.86 and 3.74 ($OCH_2$, ketoesterate), 1.55 ($CH_2$, n-propoxide), 1.38 ($CH_2$, ketoesterate), 0.95 and 1.12 ($C(CH_3)_3$, ketoesterate), 0.90 ($CH_3$, n-propoxide), 0.70 ($CH_3$, ketoesterate).

Example 10

Thermal Stability of bis(methoxy)bis(methyl 4,4-dimethyl-3-oxopentanoato)titanium A sample of bis(methoxy)bis(methyl 4,4-dimethyl-3-oxopentanoato)titanium was heated in a sealed NMR tube for one hour at 200° C. The TGA of the heated material showed ~0.2 wt % residue, similar to TGA residue of the material prior to thermal treatment. $^1$H NMR spectrum of the heated material dissolved in $d^8$-toluene showed no significant changes (FIG. 3), confirming the compositional integrity of this precursor after heating for one hour at 200° C.

Example 11

Comparison of thermal stability of bis(ethoxy)bis (ethyl 4,4-dimethyl-3-oxopentanoato) titanium and bis(ethoxy)bis(ethyl acetoacetato)titanium Samples of bis(ethoxy)bis(ethyl 4,4-dimethyl-3-oxopentanoato) titanium and bis(ethoxy)bis(ethyl acetoacetato)titanium were sealed under nitrogen atmosphere inside Perkin Elmer high pressure DSC capsules and heated at 10 C/min to 400° C. DSC data show better thermal stability of bis(ethoxy) bis(ethyl 4,4-dimethyl-3-oxopentanoato) titanium where the $R^2$ group (Formula A) is a branched alkyl (exotherm onset is 310° C.) compare to bis(ethoxy)bis(ethyl acetoacetato)titanium where $R^2$ group (Formula A) is a linear alkyl (exotherm onset is 278° C.).

Example 12

Comparison of thermal stability of bis(methoxy)bis (methyl 4,4-dimethyl-3-oxopentanoato) titanium and bis(methoxy)bis(methyl acetoacetato)titanium Samples of bis(methoxy)bis(methyl 4,4-dimethyl-3-oxopentanoato) titanium and bis(methoxy)bis(methyl acetoacetato)titanium were sealed under nitrogen atmosphere inside Perkin Elmer high pressure DSC capsules and heated at 10 C/min to 400° C. DSC data show better thermal stability of bis(ethoxy)bis(ethyl 4,4-dimethyl-3-oxopentanoato) titanium where the $R^2$ group (Formula A) is a branched alkyl (exotherm onset is 298° C.) compare to bis(ethoxy)bis(ethyl acetoacetato)titanium where $R^2$ group (Formula A) is a linear alkyl (exotherm onset is 253° C.).

Example 13

Viscosity of bis(ethoxy)bis(ethyl 4,4-dimethyl-3-oxopentanoato) titanium

Viscosity was measured using an AR-G2 rheometer (TA Instruments, New Castle, Del.). Temperature was controlled at desired temperature using a Peltier heating element. A 60 mm diameter parallel plate geometry was used. After sample loading, 600 sec was allowed for thermal equilibration before a shear rate sweep measurement. Viscosities were measured at shear rates ranging from 1 to 100 $s^{-1}$. Bis(ethoxy)bis(ethyl 4,4-dimethyl-3-oxopentanoato) titanium showed Newtonian behavior, with a viscosity of 107.9 centipoise at 25° C. and 10.1 centipoise at 80° C. The viscosity of bis(ethoxy)bis (ethyl 4,4-dimethyl-3-oxopentanoato) titanium can be decreased below 10 centipoise at 25° C. by using an additive having low viscosity, for example octane.

Example 14

Surface thermal reactivity of bis(methoxy)bis(methyl 4,4-dimethyl-3-oxopentanoato)titanium This example describes surface thermal reactivity studies using bis(methoxy)bis(methyl 4,4-dimethyl-3-oxopentanoato)titanium. The deposition temperature range is 200~400° C. The deposition chamber pressure ranges around 1.5 Torr. The container for bis(methoxy)bis(methyl 4,4-dimethyl-3-oxopentanoato)titanium was kept at 120° C. One cycle of the surface reactivity consists of 2 steps.

1. Introduce titanium precursor via bubbling with Ar as carrier gas;
2. Ar purge to remove away any left over titanium precursor with Ar;

The typical conditions are: Ti precursor pulse time was 5 seconds and the Ar purge time after Ti precursor pulse was 10 seconds. The cycle was repeated 100 times and titanium density on the substrate surface was measured by X-ray fluorescence (XRF), as shown in FIG. 7 (#1), which suggests that bis(methoxy)bis(methyl 4,4-dimethyl-3-oxopentanoato)titanium does not thermally decompose at a temperature up to at least 350° C.

Example 15

Surface thermal reactivity of bis(ethoxy)bis(ethyl 4,4-dimethyl-3-oxopentanoato)titanium This example describes surface thermal reactivity studies using bis(methoxy)bis(methyl 4,4-dimethyl-3-oxopentanoato)titanium. The deposition temperature range is 200~400° C. The deposition chamber pressure ranges around 1.5 Torr. The container for bis(methoxy)bis(methyl 4,4-dimethyl-3-oxopentanoato)titanium was kept at 150° C. One cycle of the surface reactivity consists of 2 steps.

1. Introduce titanium precursor via bubbling with Ar as carrier gas;
2. Ar purge to remove away any left over titanium precursor with Ar;

The typical conditions are: Ti precursor pulse time was 5 seconds and the Ar purge time after Ti precursor pulse was 10 seconds. The cycle was repeated 100 times and titanium density on the substrate surface was measured by XRF, as shown in FIG. 7 (#2), which suggests that bis(ethoxy)bis (ethyl 4,4-dimethyl-3-oxopentanoato)titanium does not thermally decompose at temperature up to at least 350° C.

Example 16

ALD of $TiO_2$ using bis(methoxy)bis(methyl 4,4-dimethyl-3-oxopentanoato)titanium This example describes an ALD or CCVD deposition of $TiO_2$ using bis(methoxy)bis(methyl 4,4-dimethyl-3-oxopentanoato)titanium and ozone. The deposition temperature range is 200~400° C. The deposition chamber pressure ranges around 1.5 Torr, The container for bis(methoxy)bis (methyl 4,4-dimethyl-3-oxopentanoato)titanium was kept at 120° C. One cycle of ALD or CCVD of $TiO_2$ consists of 4 steps.

1. Introduce titanium precursor via bubbling with Ar as carrier gas;
2. Ar purge to remove away any left over titanium precursor with Ar;
3. Introduce ozone into the deposition chamber, and;
4. Ar purge to remove away any unreacted ozone.

The typical ALD conditions are: Ti precursor pulse time was 4 or 8 seconds, the Ar purge time after Ti precursor pulse was 10 seconds, the ozone pulse time was 5 seconds, and the Ar purge time after ozone pulse was 10 seconds. The cycle was repeated 100 times. and $TiO_2$ films were obtained. The dependence of titanium oxide thickness on deposition temperature suggests that ALD thermal process window can be up to ~370° C. and ALD rate can be as high as 0.6 A/cycle.

Example 17

ALD of $TiO_2$ using bis(ethoxy)bis(ethyl 4,4-dimethyl-3-oxopentanoato)titanium

This example describes an ALD or CCVD deposition of $TiO_2$ using bis(ethoxy)bis(ethyl 4,4-dimethyl-3-oxopentanoato)titanium and ozone. The deposition temperature range is 200~400° C. The deposition chamber pressure ranges around 1.5 Torr. The container for bis(methoxy)bis (methyl 4,4-dimethyl-3-oxopentanoato)titanium was kept at 120° C. One cycle of ALD or CCVD of $TiO_2$ consists of 4 steps.

1. Introduce titanium precursor via bubbling with Ar as carrier gas;
2. Ar purge to remove away any left over titanium precursor with Ar;
3. Introduce ozone into the deposition chamber, and;
4. Ar purge to remove away any unreacted ozone.

The typical ALD conditions are: Ti precursor pulse time was 4 or 8 seconds, the Ar purge time after Ti precursor pulse was 10 seconds, the ozone pulse time was 5 seconds, and the Ar purge time after ozone pulse was 10 seconds. The cycle was repeated 100 times. $TiO_2$ films were obtained and the dependence of titanium oxide thickness on deposition temperature is shown in FIG. 8. The results suggests that ALD thermal process window can be up to ~375° C. with ALD rate ~0.5 A/cycle.

Example 18

ALD of $TiO_2$ using bis(ethoxy)bis(ethyl 4,4-dimethyl-3-oxopentanoato)titanium on patterned substrate This example describes an ALD deposition of $TiO_2$ using bis(ethoxy)bis(ethyl 4,4-dimethyl-3-oxopentanoato)titanium and ozone on a trench pattern wafer with a spacing of around 550 Å, an aspect ratio of 20 to 1, and silicon nitride on the surface. The deposition temperature was 375° C. The deposition chamber pressure was around 1.0 Torr. The container for bis(ethoxy)bis(ethyl 4,4-dimethyl-3-oxopentanoato)titanium was kept at 150° C. The ALD conditions: Ti precursor pulse time was 15 seconds, the Ar purge time after Ti precursor pulse was 20 seconds, the ozone pulse time was 5 seconds, and the Ar purge time after ozone pulse was 10 seconds. The cycle was repeated 200 times. FIG. 9 shows the Transmission Electron Microscope (TEM) of the deposited $TiO_2$ film with a thickness of 8.9±0.5 nm at the top of the trenches, 8.8±0.5 nm at the top corner of the trenches, 8.7±0.5 nm at middle of the trenches, and 8.2±0.5 nm at the bottom of the trenches, demonstrating excellent step coverage (>90%) from the top to the bottom of the patterned substrate.

The invention claimed is:

1. A Group 4 metal precursor represented by the formula:

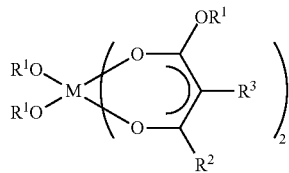

wherein M is a Group 4 metal selected from the group consisting of Ti, Zr, and Hf; wherein $R^1$ is selected from the group consisting of a linear or branched $C_{1-10}$ alkyl group and a $C_{6-12}$ aryl group; $R^2$ is selected from the group consisting of branched $C_{3-10}$ alkyl group and a $C_{6-12}$ aryl group; and $R^3$ is selected from the group consisting of hydrogen, a $C_{1-10}$ alkyl group, and a $C_{6-12}$ aryl group wherein $R^1$ in the formula is the same substituent.

2. The precursor of claim 1 wherein $R^1$ is selected from the group consisting of methyl, ethyl, and n-propyl.

3. The precursor of claim 1 wherein $R^2$ is tert-butyl.

4. The precursor of claim 3 wherein $R^3$ is hydrogen.

5. The precursor of claim 1 wherein M is zirconium and $R^1$ is selected from the group consisting of a branched $C_{3-10}$ alkyl group.

6. The precursor of claim 1, wherein M is titanium.

7. The precursor of claim 6 wherein $R^1$ is selected from the group consisting of a linear $C_{1-10}$ alkyl.

8. A titanium precursor represented by the formula:

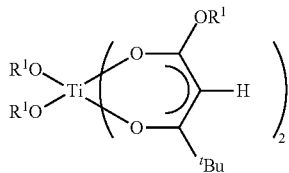

wherein $R^1$ is selected from the group consisting of methyl, ethyl, and n-propyl wherein $R^1$ in the formula is the same substituent.

9. The precursor of claim 8 where $R^1$ is methyl.

10. The precursor of claim 8 where $R^1$ is ethyl.

11. The precursor of claim 8 where $R^1$ is n-propyl.

12. A solution of the precursor of claim 1 and a solvent.

13. The solution of claim 12 wherein the solvent is selected from the group consisting of octane, ethylcyclohexane, dodecane, toluene, xylene, mesitylene, diethylbezene, and mixture thereof.

* * * * *